US010118925B2

(12) United States Patent
Griesgraber

(10) Patent No.: US 10,118,925 B2
(45) Date of Patent: Nov. 6, 2018

(54) IMIDAZO[4,5-C] RING COMPOUNDS CONTAINING SUBSTITUTED GUANIDINE GROUPS

(71) Applicant: 3M INNOVATIVE PROPERTIES COMPANY, St. Paul, MN (US)

(72) Inventor: George W. Griesgraber, Eagan, MN (US)

(73) Assignee: 3M Innovative Properties Company, St. Paul, MN (US)

(*) Notice: Subject to any disclaimer, the term of this patent is extended or adjusted under 35 U.S.C. 154(b) by 0 days.

(21) Appl. No.: 15/753,573

(22) PCT Filed: Aug. 26, 2016

(86) PCT No.: PCT/US2016/048831
§ 371 (c)(1),
(2) Date: Feb. 20, 2018

(87) PCT Pub. No.: WO2017/040234
PCT Pub. Date: Mar. 9, 2017

(65) Prior Publication Data
US 2018/0244669 A1    Aug. 30, 2018

Related U.S. Application Data

(60) Provisional application No. 62/211,896, filed on Aug. 31, 2015.

(51) Int. Cl.
*C07D 471/04* (2006.01)
*A61K 31/437* (2006.01)
(52) U.S. Cl.
CPC ................ *C07D 471/04* (2013.01)
(58) Field of Classification Search
CPC .. C07D 471/04; C07D 471/12; A61K 31/437; A61K 31/4375
USPC .......................................... 546/82; 514/293
See application file for complete search history.

(56) References Cited

U.S. PATENT DOCUMENTS

| | | | |
|---|---|---|---|
| 4,689,338 A | 8/1987 | Gerster | |
| 5,352,784 A | 10/1994 | Nikolaides et al. | |
| 5,446,153 A | 8/1995 | Lindstrom et al. | |
| 6,039,969 A | 3/2000 | Tomai et al. | |
| 6,069,149 A | 5/2000 | Nanba et al. | |
| 6,110,929 A | 8/2000 | Gerster et al. | |
| 6,194,425 B1 | 2/2001 | Gerster et al. | |
| 6,200,592 B1 | 3/2001 | Tomai et al. | |
| 6,331,539 B1 | 12/2001 | Crooks et al. | |
| 6,451,810 B1 | 9/2002 | Coleman et al. | |
| 6,573,273 B1 | 6/2003 | Crooks et al. | |
| 6,664,264 B2 | 12/2003 | Dellaria et al. | |
| 6,677,349 B1 | 1/2004 | Griesgraber | |
| 6,784,188 B2 | 8/2004 | Crooks et al. | |
| 6,800,624 B2 | 10/2004 | Crooks et al. | |
| 6,888,000 B2 | 5/2005 | Crooks et al. | |
| 7,115,622 B2 | 10/2006 | Crooks et al. | |
| 7,163,947 B2 | 1/2007 | Griesgraber et al. | |
| 7,393,859 B2 | 7/2008 | Coleman et al. | |
| 7,544,697 B2 | 6/2009 | Hays et al. | |
| 7,579,359 B2 | 8/2009 | Krepski et al. | |
| 7,799,800 B2 | 9/2010 | Wightman | |
| 7,884,207 B2 | 2/2011 | Stoermer et al. | |
| 7,915,281 B2 | 3/2011 | Moser et al. | |
| 7,968,563 B2 | 6/2011 | Kshirsagar et al. | |
| 8,088,790 B2 | 1/2012 | Kshirsagar et al. | |
| 8,168,802 B2 | 5/2012 | Hays et al. | |
| 8,673,932 B2 | 3/2014 | Kshirsagar et al. | |
| 8,691,837 B2 | 4/2014 | Krepski et al. | |
| 8,697,873 B2 | 4/2014 | Krepski et al. | |
| 8,728,486 B2 | 5/2014 | David et al. | |
| 9,034,336 B2 | 5/2015 | Ferguson et al. | |
| 2009/0005376 A1 | 1/2009 | Krepski et al. | |
| 2011/0269965 A1 | 11/2011 | Hays et al. | |
| 2013/0230578 A1 | 9/2013 | Wightman | |

FOREIGN PATENT DOCUMENTS

WO    WO 2005/051380    6/2005
WO    WO 2017/040233    3/2017

OTHER PUBLICATIONS

Berge, S.M. et al.; "Pharmaceutical Salts"; Journal of Pharmaceutical Sciences; vol. 66, No. 1; 1977; pp. 1-19.
Bernatowicz, M.S. et al.; "1H-Pyrazole-a-carboxamidine Hydrochloride: An Attractive Reagent for Guanylation of Amines and Its Application to Peptide Synthesis"; J. Org. Chem; vol. 47; 1992; pp. 2497-2502.
Bernatowicz, M.S. et al.; "Urethane Protected Derivatives of 1-Guanylpyrazole for the Mild and Efficient Preparation of Guanidines"; Tetrahedron Letters; vol. 34, No. 21, 1993; pp. 3389-3392.
Katritzky, A.R. et al.; "Recent developments in guanylating agents"; ARKIVOC; 2005; pp. 49-87.
Lee, Y. et al.; "Solid-Phase Syntheses of $N^\omega$Propylarginine-Containing Dipeptides, Dipeptide Esters, and Dipeptide Amides"; Synthesis; No. 51; 1999; pp. 1495-1499.
Lee, Y. et al.; "1H-Pyrazole-l-carboxamidines: New Inhibitors of Nitric Oxide Synthase"; Biorganic & Medicinal Chemistry Letters; vol. 10; 2000; pp. 2771-2774.
Maryanoff, C.A. et al.; "A Convenient Synthesis of Guanidines from Thioureas" J. Org. Chem.; vol. 51; 1986; pp. 1882-1884.
Shukla, N.M. et al.; "Structure-Activity Relationships in Human Toll-Like Receptor 7-Active Imidazoquinoline Analogues" Journal of Medicinal Chemistry; vol. 53; 2010; pp. 4450-4465 (XP055081984).
Zhang, W. et al.; "Recent development of synthetic preparation methods for guanidines via transition metal catalysis"; Chem. Commun.; vol. 51, 2015; pp. 254-265.

*Primary Examiner* — Charanjit Aulakh
(74) *Attorney, Agent, or Firm* — Eric Silverman

(57) ABSTRACT

Imidazo[4,5-c] ring compounds, (particularly imidzao[4,5-c]quinolines, 6,7,8,9-tetrahydroimidazo[4,5-c]quinolines, imidazo[4,5-c]naphthyridines, and 6,7,8,9-tetrahydroimidazo[4,5-c]naphthyridine compounds) having a substituted guanidine substituent at the 1-position, pharmaceutical compositions containing the compounds, and methods of making the compounds are disclosed. Methods of use of the compounds as immune response modifiers, for inducing cytokine biosynthesis in animals and in the treatment of diseases including viral and neoplastic diseases are also disclosed.

20 Claims, No Drawings

IMIDAZO[4,5-C] RING COMPOUNDS CONTAINING SUBSTITUTED GUANIDINE GROUPS

CROSS REFERENCE TO RELATED APPLICATIONS

This application is a national stage filing under 35 U.S.C. 371 of PCT/US2016/048831, filed Aug. 26, 2016, which claims the benefit of U.S. Provisional Patent Application No. 62/211,896, filed Aug. 31, 2015, the disclosure of which is incorporated by reference in its entirety herein.

BACKGROUND

Some drug compounds act by stimulating certain key aspects of the immune system, as well as by suppressing certain other aspects (e.g., U.S. Pat. Nos. 6,039,969 and 6,200,592). These compounds are sometimes referred to as immune response modifiers (IRMs). Some IRM compounds are useful for treating viral diseases, neoplasias, and $T_H2$-mediated diseases; some are useful as vaccine adjuvants.

IRM compounds have been reported based on the following bicyclic and tricyclic ring systems: 1H-imidazo[4,5-c]quinolin-4-amines (e.g., U.S. Pat. No. 4,689,338); 1H-imidazo[4,5-c]pyridin-4-amines (e.g., U.S. Pat. No. 5,446,153); 1H-imidazo[4,5-c][1,5]naphthyidin-4-amines (e.g., U.S. Pat. No. 6,194,425); thiazolo[4,5-c]quinolone-4-amines and oxazolo[4,5-c]quinolone-4-amines (e.g., U.S. Pat. No. 6,110,929); 6,7,8,9-1H-tetrahydro-1H-imidazo[4,5-c]quinolin-4-amines (e.g., U.S. Pat. No. 5,352,784); 2H-pyrazolo[3,4-c]quinolin-4-amines (e.g., U.S. Pat. No. 7,544,697); and N-1 and 2-substituted 1H-imidazo[4,5-c]quinolin-4-amines (e.g., U.S. Pat. Nos. 6,331,539, 6,451,810, 6,664,264, 8,691,837, 8,088,790, 8,673,932, 8,697,873, 7,915,281).

SUMMARY

New compounds that can be useful in inducing cytokine biosynthesis in animals are disclosed. Such compounds are of the following Formulas I, II, and XIV:

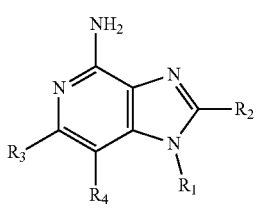

Formula I

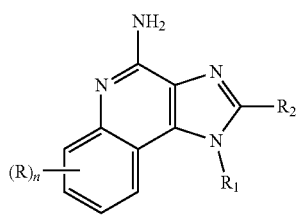

Formula II

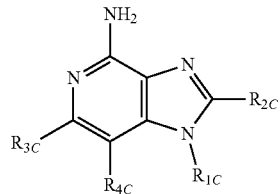

Formula XIV wherein $R_1$, $R_2$, $R_3$, $R_4$, R, $R_{1C}$, $R_{2C}$, $R_{3C}$, $R_{4C}$, and n are as defined below. A common structural feature of the compounds of Formulas I, II, and XIV is the inclusion of a substituted guanidino substituent as a component of $R_1$ and $R_{1C}$.

In addition, more specific examples of such compounds include the compounds of Formulas III-XIII and Formulas XV-XVIII which are defined below, as well as salts, particularly pharmaceutically acceptable salts, thereof.

The compounds and salts, such as pharmaceutically acceptable salts, of Formulas I-XVIII can be useful as immune response modifiers due to their ability to induce cytokine biosynthesis (e.g., induce the synthesis of at least one cytokine) and otherwise modulate the immune response when administered to animals. The compounds can therefore be useful in the treatment of a variety of conditions such as viral diseases and tumors that are responsive to such changes in the immune response.

Pharmaceutical compositions containing an effective amount of one or more compounds of Formulas I-XVIII and salts, particularly pharmaceutically acceptable salts, thereof are disclosed. Also disclosed are methods of inducing cytokine biosynthesis in an animal, treating a viral disease in an animal, and treating a neoplastic disease in an animal by administering to the animal one or more compounds from Formulas I-XVIII and/or pharmaceutically acceptable salts thereof.

Methods for synthesizing compounds of Formulas I-XVIII are provided.

The above summary of the present invention is not intended to describe each disclosed embodiment or every implementation of the present invention. The description that follows more particularly exemplifies illustrative embodiments. In several places throughout the description, guidance is provided through lists of examples, which can be used in various combinations. In each instance, the recited list serves only as a representative group and should not be interpreted as an exhaustive list.

DETAILED DESCRIPTION

As used herein, "a", "an", "the", "at least one", and "one or more" are used interchangeably and are intended to include both the singular and the plural except in cases where the singular alone is specifically called for or clearly required by the context.

As used herein, "preferred" and "preferably" refer to embodiments of the disclosure that may afford certain benefits, under certain circumstances. However, other embodiments may also be preferred, under the same or other circumstances. Furthermore, the recitation of one or more preferred embodiments does not imply that other embodiments are not useful, and is not intended to exclude other embodiments from the scope of the invention.

"Ph" is used as an abbreviation for a phenyl group.

As used herein, "pharmaceutically acceptable carriers" include those carriers that can deliver therapeutically effective amounts of one or more of the compounds or salts of the disclosure to a subject by a chosen route of administration, are generally tolerated by the subject, and have an acceptable toxicity profile (preferably minimal to no toxicity at an administered dose). Some suitable pharmaceutically acceptable carriers are described in Remington's Pharmaceutical Sciences, 18$^{th}$ Edition (1990), Mack Publishing Co. and can be readily selected by one of ordinary skill in the art.

"Therapeutically effective amount" and "effective amount" are defined as an amount of compound or salt sufficient to induce a therapeutic or prophylactic effect, such a cytokine induction, immunomodulation, antitumor activity, and/or antiviral activity.

"Independently," when used to describe the identity of one or more variable reference elements (such as when used in the phrase "independently selected" or "independently selected from the group"), means that each occurrence of any of the variable elements may have the same or different identity, within the specified limitations, regardless of the identity of any other occurrence of the reference element(s). Thus, if there are two occurrences of reference element "A," and reference element "A" can be independently selected from identity "B" or identity "C", each of the two occurrences of "A" can be either "B" or "C", in any combination (e.g., "B,B"; "B,C"; "C,B"; or "C,C"). Alternatively, if there are two different reference elements (reference element "D" and reference element "E") that can occur together and reference element "D" and reference element "E" can each be independently selected from identity "F" or identity "G", then each occurrence of "D" can be "F" or "G" and likewise each occurrence of "E" can be "F" or "G", to produce any combination of "D" and "E" (e.g., "D"="F" and "E"="F"; "D"="F" and "E"="G"; "D"="G" and "E"="F"; or "D"="G" and "E"="G".

The terms "alkyl", "alkenyl", "alkynyl" and the prefix "alk-" are inclusive of straight chain groups, branched chain groups, cyclic groups, and combinations thereof, e.g. cycloalkyl and cycloalkenyl. Alkyl groups are saturated aliphatic hydrocarbons. Alkenyl groups are unsaturated aliphatic hydrocarbons having one or more carbon-carbon double bonds. Alkynyl groups are unsaturated aliphatic hydrocarbons having one or more carbon-carbon triple bonds. Unless otherwise specified, these groups contain from 1 to 14 carbon atoms, with alkenyl groups containing from 2 to 14 carbon atoms and alkynyl groups containing from 2-14 atoms. In some embodiments, these groups have a total of up to 14 carbon atoms, up to 12 carbon atoms, up to 10 carbon atoms, up to 8 carbon atoms, up to 6 carbon atoms, up to 5 carbon atoms, up to 4 carbon atoms, up to 3 carbon atoms, or up to 2 carbon atoms. In some embodiments, these groups have at least 1 carbon atom, at least 2 carbon atoms, at least 3 carbon atoms, or at least 4 carbon atoms. Cyclic groups can be monocyclic or polycyclic and preferably have from 3 to 10 ring carbon atoms. Exemplary cyclic groups include cyclopropyl, cyclopropylmethyl, cyclobutyl, cyclobutylmethyl, cyclopentyl, cyclopentylmethyl, cyclohexyl, cyclohexylmethyl, adamantyl, and substituted and unsubstituted bornyl, norbornyl, norbornenyl, and the like The term "haloalkyl" is inclusive of alkyl groups that are substituted by one or more halogen atoms, including perfluorinated groups. This is also true of other groups that include the prefix "halo-". Examples of suitable haloalkyl groups are chloromethyl, trifluoromethyl, pentafluoroethyl and the like.

Unless otherwise specified, "alkylene", "alkenylene", and "alkynylene" are the diradical equivalents of the "alkyl", "alkenyl", and "alkynyl" defined above. The terms, "alkylenyl", "alkenylenyl", and "alkynylenyl" are used when "alkylene", "alkenylene", and "alkynylene" respectively, are substituted. For example, an alkoxyalkylenyl group comprises an alkylene moiety to which an alkoxy group is attached (e.g., —CH$_2$OCH$_3$, —CH$_2$CH$_2$OCH$_3$, —CH$_2$OCH$_2$CH$_3$, etc.). As a further example, a hydroxyalkylenyl group comprises an alkylene moiety to which a hydroxyl group is attached (e.g., —CH$_2$OH, —CH$_2$CH$_2$OH, etc.). As yet another example arylalkylenyl group comprises an alkylene moiety to which an aryl group is attached [e.g., —CH$_2$Ph, —CH$_2$CH$_2$Ph, etc.].

An alkylene group with carbon atoms optionally "interrupted" by one or more —O— groups refers to having carbon atoms on either side of the —O—. Examples include —CH$_2$CH$_2$—O—CH$_2$CH$_2$—, —CH$_2$—CH$_2$—O—CH$_2$—CH$_2$—O—CH$_2$CH$_2$—, —(CH$_2$)$_{2-4}$—(OCH$_2$CH$_2$—)$_{1-5}$, —(CH$_2$)$_{2-6}$—(OCH$_2$CH$_2$—)$_{1-4}$, etc.

Some examples of alkylamino groups include —NHCH$_3$, —NHCH$_2$CH$_3$, —NHCH(CH$_3$)$_2$, etc. It is understood that the two alkyl groups of a dialkylamino group can be the same or different alkyl groups. Some examples of dialkylamino groups include —N(CH$_3$)$_2$, —N(CH$_2$CH$_3$)$_2$, —N(CH$_3$)(CH$_2$CH$_3$), —N(CH$_3$)(CH$_2$CH$_2$CH$_3$), etc.

Some examples of alkylaminoalkylenyl groups include —CH$_2$NHCH$_3$, —CH$_2$NHCH$_2$CH$_3$, —CH$_2$CH$_2$NHCH$_3$, etc.

Some examples of benzyloxyalkylenyl groups include —CH$_2$OCH$_2$Ph, —CH$_2$CH$_2$OCH$_2$Ph, —CH$_2$CH$_2$CH$_2$OCH$_2$Ph, etc.

Some examples of —C(O)—O-alkyl include —C(O)—O—CH$_3$, —C(O)—O—CH$_2$CH$_3$, —C(O)—O—CH$_2$CH$_2$CH$_3$, —C(O)—O—C(CH$_3$)$_3$, etc.

The term "aryl" as used herein includes carbocyclic aromatic rings or ring systems. Examples of aryl groups include phenyl (designated by the abbreviation "Ph" herein), naphthyl, and biphenyl.

The term "heteroaryl" includes aromatic rings or ring systems that contain at least one ring heteroatom (e.g. O, S, N). In some embodiments, the term "heteroaryl" includes a ring or ring system that contains 2-12 carbon atoms, 1-3 rings, 1-4 heteroatoms, with O, S, and N as the heteroatoms. Exemplary heteroaryl groups include furyl, thienyl, pyridyl, quinolinyl, isoquinolinyl, indolyl, isoindolyl, triazolyl, pyrrolyl, tetrazolyl, imidazolyl, pyrazolyl, oxazolyl, thiazolyl, benzofuranyl, benzothiophenyl, quinoxalinyl, benzothiazolyl, napthyridinyl, ixoxazolyl, isothiazolyl, purinyl, quinazolinyl, pyrazinyl, 1-oxidopyridyl, pyridazinyl, triazinyl, tetrazinyl, oxadiazolyl, thiadiazolyl, and the like. Preferred heteroaryl groups include, thienyl, pyridyl, quinolinyl, indolyl and imidazolyl.

The terms "arylene", "-arylene-", "heteroarylene", and "-heteroarylene-" are the diradical equivalents of the "aryl" and "heteroaryl" groups defined above. The terms "arylenyl" and "heteroarylenyl" are used when "arylene" and "heteroarylene" are substituted. For example an alkylarylenyl group comprises an arylene moiety to which an alkyl group is attached (e.g., -Ph-CH$_3$).

The term "compound" includes not only the specific structural formula as drawn or named, but also its configurational isomers, stereoisomers, such as enantiomers, diastereomers, and meso isomers, as well as combinations of one or more of any of the foregoing, except in cases when a specific isomer, enantiomer, or the like is specifically called out. For those structures that exist as tautomers, the term "compound" is intended to include all tautomers, even when only one is drawn, unless only a single tautomer is explicitly recited. For structures that are able to form salts, "compound" also includes salts, unless a "free" or "free base" form, which refers to non-salt forms, of the compound is specifically recited. Particular salts are pharmaceutically acceptable salts, such as those described in Berge, Stephen M., "Pharmaceutical Salts", *Journal of Pharmaceutical Sciences*, 1977, 66, pages 1-19. Salts can be prepared by reacting a free compound (that is, one not in a salt form) with an inorganic or organic acid such as, for example, hydrochloric acid, sulfuric acid, hydrobromic acid, methane sulfonic acid, ethane sulfonic acid, malic acid, maleic acid, acetic acid, trifluoroacetic acid, para-toluenesulfonic acid, salicylic acid, succinic acid, tartaric acid, citric acid, pamoic acid, xinafoic acid, oxalic acid, and the like. Typical pharmaceutically acceptable salts include hydrochloride and dihydrochloride.

This disclosure provides compounds of the following Formula I:

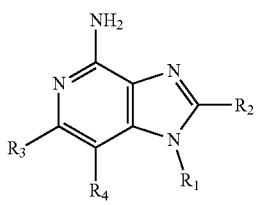

Formula I wherein $R_1$, $R_2$, $R_3$, and $R_4$ are as defined below; and pharmaceutically acceptable salts thereof.

Examples of compounds of Formula I are more specifically defined by the following Formulas II-V:

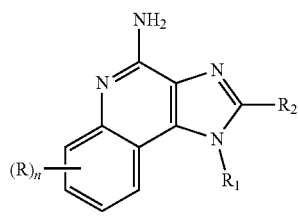

Formula II

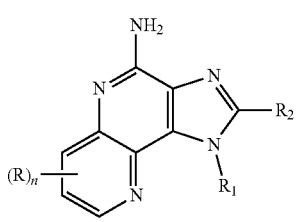

Formula III

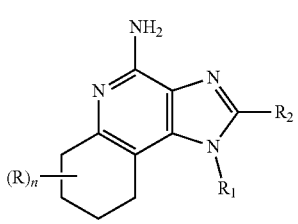

Formula IV

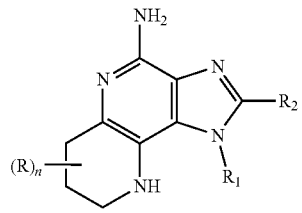

Formula V wherein R, $R_1$, $R_2$, and n are as defined below as well as salts, particularly pharmaceutically acceptable salts, thereof.

For compounds and salts, such as pharmaceutically acceptable salts, of Formula I, $R_3$ and $R_4$ are taken together to form a fused benzene ring, a fused pyridine ring, a fused cyclohexene ring, or a fused tetrahydropyridine ring; wherein the fused benzene ring, fused pyridine ring, fused cyclohexene ring, or fused tetrahydropyridine ring is either unsubstituted or substituted by one or more R groups.

For compounds and salts, such as pharmaceutically acceptable salts, of Formulas I-V: R is selected from the group consisting of halogen, hydroxyl, alkyl, alkoxy, haloalkyl, —C(O)—O-alkyl, —C(O)—O—CH$_2$Ph, —C(O)—O-aryl, amino, alkylamino, and dialkylamino, aryl, arylalkylenyl, aryloxyalkylenyl, arylalkyleneoxy, aryloxy, heteroaryl, heteroarylalkylenyl, heteroaryloxyalkylenyl, heteroarylalkyleneoxy, and heteroaryloxy, wherein the alkyl, aryl, arylalkylenyl, aryloxyalkylenyl, arylalkyleneoxy, aryloxy, heteroaryl, heteroarylalkylenyl, heteroaryloxyalkyenyl, heteroarylalkyleneoxy, and heteroaryloxy groups can be unsubstituted or substituted by one or more substituents independently selected from the group consisting of alkyl, alkoxy, halogen, haloalkyl, hydroxyl, hydroxyalkylenyl, alkoxyalkylenyl, arylalkyleneoxy, and nitrile;

n is an integer from 0 to 2;

$R_1$ is selected from the group consisting of —W—X—N(R$_7$)—C(=N—R$_5$)—N(H)R$_6$, —W—Z—N(R$_7$)—C(=N—R$_5$)—N(H)R$_6$, and

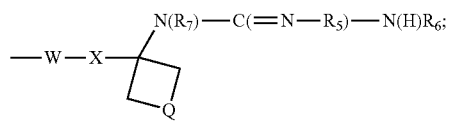

W is selected from the group consisting of a covalent bond, —O—, and —NH—;

X is selected from the group consisting of alkylene, alkenylene, and alkynylene, wherein any of the alkylene, alkenylene, and alkynylene groups can be optionally interrupted by one or more —O— groups;

Z is selected from the group consisting of
—X-arylene-X—,
—X-heteroarylene-X—,
—X-arylene-, and
—X-heteroarylene-;

$R_2$ is selected from the group consisting of hydrogen, alkyl, alkenyl, alkynyl, —O-alkyl, hydroxyalkylenyl, alkoxyalkylenyl, alkylaminoalkylenyl, hydroxyl, —CH$_2$—NH—O-alkyl, and —CH$_2$NHC(O)-alkyl;

$R_7$ is selected from the group consisting of hydrogen, alkyl, arylalkylenyl, alkoxyalkylenyl, aryloxyalkylenyl, benzyloxyalkylenyl, aryl-(CH$_2$)$_{2-6}$—O-alkylenyl, and cycloalkylalkylenyl; wherein any of the alkyl, arylalkylenyl, alkoxyalkylenyl, aryloxyalkylenyl, benzyloxyalkylenyl, aryl- (CH$_2$)$_{2-6}$—O-alkylenyl, and cycloalkylalkylenyl groups can be either unsubstituted or substituted with one or more substituents selected from the group consisting of halogen, hydroxyl, alkyl, alkoxy, haloalkyl, and nitrile;

Q is selected from the group consisting of a covalent bond, —CH$_2$—, —CH$_2$CH$_2$—, —CH$_2$CH$_2$CH$_2$—, —CH$_2$CH$_2$CH$_2$CH$_2$—, —CH$_2$CH$_2$CH$_2$CH$_2$CH$_2$—, —CH$_2$—O—CH$_2$—, and —OCH$_2$—;

R$_5$ and R$_6$ are independently selected from the group consisting of hydrogen, —C(O)—O-alkyl, alkyl, cycloalkyl, aryl, arylalkylenyl, aryloxyalkylenyl, heteroaryl, heteroarylalkylenyl, heteroaryloxyalkylenyl, cycloalkylalkylenyl, aryl-(CH$_2$)$_{2-6}$—O-alkylenyl, and benzyloxyalkylenyl; wherein any of the alkyl, cycloalkyl, aryl, arylalkylenyl, aryloxyalkylenyl, heteroaryl, heteroarylalkylenyl, heteroaryloxyalkylenyl, cycloalkylalkylenyl, aryl-(CH$_2$)$_{2-6}$—O-alkylenyl, and benzyloxyalkylenyl groups can be either unsubstituted or substituted with one or more substituents independently selected from the group consisting of halogen, hydroxyl, alkoxy, alkyl, haloalkyl, cycloalkyl, nitrile, aryl, heteroaryl, and dialkylamino; with the proviso that R$_5$ and R$_6$ are not both hydrogen.

In some embodiments of Formula I, R$_3$ and R$_4$ are taken together to form a fused benzene ring, a fused pyridine ring, or a fused cyclohexene ring.

In some embodiments of Formula I, R$_3$ and R$_4$ are taken together to form a fused benzene ring or a fused cyclohexene ring.

In some embodiments of Formula I, R$_3$ and R$_4$ are taken together to form a fused benzene ring or a fused pyridine ring.

In some embodiments of Formula I, R$_3$ and R$_4$ are taken together to form a fused benzene ring.

In some embodiments of Formula I, R$_3$ and R$_4$ are taken together to form a fused benzene ring, a fused pyridine ring, or a fused cyclohexene ring; wherein the fused benzene ring, fused pyridine ring, or fused cyclohexene ring is either unsubstituted or substituted by one and only one R group.

In some embodiments of Formula I, R$_3$ and R$_4$ are taken together to form a fused benzene ring or a fused pyridine ring; wherein the fused benzene ring or fused pyridine ring is either unsubstituted or substituted by one and only one R group.

In some embodiments of Formulas II-V, n is 0 or 1.

In some embodiments of Formulas II-V, n is 0.

In some embodiments of Formulas I-V, R is selected from the group consisting of halogen, hydroxyl, alkyl, alkoxy, haloalkyl, —C(O)—O-alkyl, —C(O)—OCH$_2$Ph, —C(O)—O-aryl, amino, alkylamino, and dialkylamino.

In some embodiments of Formulas I-V, R is selected from the group consisting of hydroxyl, F, Cl, —CF$_3$, —O—C$_{1-6}$alkyl, and —C$_{1-6}$alkyl.

In some embodiments of Formulas I-V, R is selected from the group consisting of hydroxyl, F, Cl, —CF$_3$, —OCH$_3$, —OCF$_3$, —OCH$_2$CH$_3$, —OCH(CH$_3$)$_2$, —CH$_3$, —CH$_2$CH$_3$, —CH$_2$CH$_2$CH$_3$, and —CH(CH$_3$)$_2$.

In some embodiments of Formulas I-V, R is —C(O)OC$_{1-4}$alkyl.

In some embodiments of Formulas I-V, R is selected from the group consisting of —CO$_2$CH$_3$, —CO$_2$CH$_2$CH$_3$, —CO$_2$CH(CH$_3$)$_2$, —CO$_2$CH$_2$CH$_2$CH$_3$, —CO$_2$CH$_2$CH$_2$CH$_2$CH$_3$, —CO$_2$—CH$_2$Ph, and —CO$_2$CH$_2$CH(CH$_3$)$_2$.

In some embodiments of Formulas I-V, R$_2$ is selected from the group consisting hydrogen, alkyl, alkoxyalkylenyl, alkylaminoalkylenyl, and hydroxyalkylenyl.

In some embodiments of Formulas I-V, R$_2$ is selected from the group consisting hydrogen, alkyl, and alkoxyalkylenyl.

In some embodiments of Formulas I-V, R$_2$ is selected from the group consisting of hydrogen, —CH$_3$, —CH$_2$CH$_3$, —CH$_2$CH$_2$CH$_3$, —CH$_2$CH$_2$CH$_2$CH$_3$, —CH$_2$OCH$_3$, —CH$_2$OCH$_2$CH$_3$, —CH$_2$CH$_2$OCH$_3$, —CH$_2$NHCH$_3$, —CH$_2$NHCH$_2$CH$_3$, —CH$_2$CH$_2$NHCH$_3$, —CH$_2$OH, —CH$_2$CH$_2$OH, and —CH$_2$NHOCH$_3$.

In some embodiments of Formulas I-V, R$_2$ is selected from the group consisting of hydrogen, —CH$_3$, —CH$_2$CH$_3$, —CH$_2$CH$_2$CH$_3$, —CH$_2$CH$_2$CH$_2$CH$_3$, —CH$_2$OCH$_3$, —CH$_2$OCH$_2$CH$_3$, and —CH$_2$CH$_2$OCH$_3$.

In some embodiments of Formulas I-V, R$_2$ is —CH$_2$NHC(O)CH$_3$ or —CH$_2$NHC(O)cyclopropyl.

In some embodiments of Formulas I-V, —CH$_2$NHC(O)C$_{1-3}$alkyl.

In some embodiments of Formulas I-V, R$_7$ is hydrogen, C$_{1-8}$alkyl, or —CH$_2$Ph.

In some embodiments of Formulas I-V, R$_7$ is hydrogen or C$_{1-4}$alkyl.

In some embodiments of Formulas I-V, R$_7$ is hydrogen.

In some embodiments of Formulas I-V, R$_7$ is selected from the group consisting of hydrogen, —CH$_3$, —CH$_2$CH$_3$, —CH(CH$_3$)$_2$, —CH$_2$CH$_2$CH$_3$, —CH$_2$CH$_2$CH$_2$CH$_3$, —CH$_2$CH(CH$_3$)$_2$, —C(CH$_3$)$_3$, —CH$_2$CH$_2$CH$_2$CH$_3$, —CH$_2$CH$_2$CH(CH$_3$)$_2$, cyclopentyl, -cyclohexyl, —CH$_2$(cyclopentyl), —CH$_2$(cyclohexyl), and —CH$_2$CH$_2$—O—CH$_3$.

In some embodiments of Formulas I-V, R$_7$ is selected from the group consisting of hydrogen, alkyl, —CH$_2$Ph, —CH$_2$CH$_2$Ph, —CH$_2$CH$_2$—O-Ph, —CH$_2$CH$_2$—O—CH$_2$Ph, and —(CH$_2$)$_{2-6}$—O—(CH$_2$)$_{1-6}$Ph, wherein Ph can be either unsubstituted or substituted with one or more substituents selected from the group consisting of halogen, hydroxyl, alkyl, alkoxy, haloalkyl, and nitrile.

In some embodiments of Formulas I-V, W is a covalent bond or —O—.

In some embodiments of Figures I-V, W is a covalent bond.

In some embodiments of Formulas I-V, X is alkylene optionally interrupted by one or more —O— groups.

In some embodiments of Formulas I-V, X is a C$_{2-12}$alkylene optionally interrupted by one or more —O— groups.

In some embodiments of Formulas I-V, X is C$_{2-8}$alkylene.

In some embodiments of Formulas I-V, X is C$_{2-6}$alkylene.

In some embodiments of Formulas I-V, X is C$_{2-5}$alkylene.

In some embodiments of Formulas I-V, X is a C$_{2-8}$alkylene optionally interrupted by one or more —O— groups.

In some embodiments of Formulas I-V, X is selected from the group consisting of —CH$_2$CH$_2$—, —CH$_2$CH$_2$CH$_2$—, —CH$_2$CH$_2$CH$_2$CH$_2$—, —CH$_2$CH$_2$CH$_2$CH$_2$CH$_2$—, —CH$_2$CH$_2$CH$_2$CH$_2$CH$_2$CH$_2$—, —CH$_2$CH$_2$CH$_2$CH$_2$CH$_2$CH$_2$CH$_2$—, —CH$_2$CH$_2$CH$_2$CH$_2$CH$_2$CH$_2$CH$_2$CH$_2$—, —CH$_2$C(CH$_3$)$_2$—, —CH$_2$C(CH$_3$)$_2$CH$_2$—, —CH$_2$CH$_2$—O—CH$_2$CH$_2$—, —CH$_2$CH$_2$—O—CH$_2$CH$_2$—O—CH$_2$CH$_2$—, —(CH$_2$)$_{2-4}$—(OCH$_2$CH$_2$—)$_{1-5}$, and —(CH$_2$)$_{2-6}$—(OCH$_2$CH$_2$—)$_{1-4}$.

In some embodiments of Formulas I-V, Z is —C$_{1-5}$alkylene-arylene-C$_{1-5}$alkylene- or —C$_{1-5}$alkylene-heteroarylene-C$_{1-5}$alkylene-.

In some embodiments of Formulas I-V, Z is —CH$_2$-phenylene-CH$_2$—.

In some embodiments of Formulas I-V, R$_1$ is selected from the group consisting of —W—X—N(H)—C(=N—R$_5$)—N(H)R$_6$, and —W—Z—N(H)—C(=N—R$_5$)—N(H)R$_6$.

In some embodiments of Formulas I-V, $R_1$ is —X—N(H)—C(=N—$R_5$)—N(H)$R_6$.

In some embodiments of Formulas I-V, $R_5$ and $R_6$ are independently selected from the group consisting of hydrogen, alkyl, phenyl, and phenylalkylenyl; wherein $R_5$ and $R_6$ are not both hydrogen.

In some embodiments of Formulas I-V, $R_5$ and $R_6$ are independently selected from the group consisting of hydrogen, alkyl, cycloalkyl, cycloalkylalkylenyl, aryl, and arylalkylenyl; wherein $R_5$ and $R_6$ are not both hydrogen.

In some embodiments of Formulas I-V, $R_5$ and $R_6$ are independently selected from the group consisting of hydrogen, alkyl, cycloalkyl, aryl, arylalkylenyl, aryloxyalkylenyl, heteroaryl, heteroarylalkylenyl, heteroaryloxyalkylenyl, cycloalkylalkylenyl aryl-$(CH_2)_{2-6}$—O-alkylenyl, and benzyloxyalkylenyl; wherein any of the alkyl, cycloalkyl, aryl, arylalkylenyl, aryloxyalkylenyl, heteroaryl, heteroarylalkylenyl, heteroaryloxyalkylenyl, cycloalkylalkylenyl, aryl-$(CH_2)_{2-6}$—O-alkylenyl, and benzyloxyalkylenyl groups can be either unsubstituted or substituted with one or more substituents independently selected from the group consisting of halogen, hydroxyl, alkoxy, alkyl, haloalkyl, cycloalkyl, nitrile, aryl, heteroaryl, and dialkylamino; with the proviso that $R_{5A}$ and $R_{6A}$ are not both hydrogen.

In some embodiments of Formulas I-V, $R_5$ and $R_6$ are independently selected from the group consisting of alkyl, cycloalkyl, aryl, arylalkylenyl, aryloxyalkylenyl, heteroaryl, heteroarylalkylenyl, heteroaryloxyalkylenyl, cycloalkylalkylenyl, aryl-$(CH_2)_{2-6}$—O-alkylenyl, and benzyloxyalkylenyl; wherein any of the alkyl, cycloalkyl, aryl, arylalkylenyl, aryloxyalkylenyl, heteroaryl, heteroarylalkylenyl, heteroaryloxyalkylenyl, cycloalkylalkylenyl, aryl-$(CH_2)_{2-6}$—O-alkylenyl, benyloxyalkylenyl groups can be either unsubstituted or substituted with one or more substituents independently selected from the group consisting of halogen, hydroxyl, alkoxy, alkyl, haloalkyl, cycloalkyl, nitrile, aryl, heteroaryl, and dialkylamino.

In some embodiments of Formulas I-V, $R_5$ and $R_6$ are independently selected from the group consisting of hydrogen, —$CH_3$, —$CH_2CH_3$, —$CH(CH_3)_2$, —$CH_2CH_2CH_3$, —$CH_2CH_2CH_2CH_3$, —$CH_2CH(CH_3)_2$, —$C(CH_3)_3$, —$CH_2CH_2CH_2CH_2CH_3$, —$(CH_2)_{5-9}CH_3$, —$CH_2CH_2CH(CH_3)_2$, cyclopropyl, cyclopentyl, cyclohexyl, —$CH_2$-cyclopropyl, —$CH_2$-cyclopentyl, —$CH_2$-cyclohexyl, —$CH_2CH_2$—O—$CH_3$, —$(CH_2)_{3-8}$—O—$CH_3$, and —$CH_2CH_2CH_2N(CH_3)_2$; and wherein $R_5$ and $R_6$ are not both hydrogen.

In some embodiments of Formulas I-V, $R_5$ and $R_6$ are independently selected from the group consisting of hydrogen, alkyl, -Ph, —$CH_2$Ph, —$CH_2CH_2$Ph, —$(CH_2)_{3-8}$Ph, —$CH_2CH_2$—O-Ph, —$(CH_2)_{3-8}$OPh, —$CH_2CH_2$—O—$CH_2$Ph, —$(CH_2)_{3-8}OCH_2$Ph, and —$(CH_2)_{2-8}$—O—$(CH_2)_{1-4}$Ph, wherein the Ph group can be either unsubstituted or substituted with one or more substituents independently selected from the group consisting of halogen, hydroxyl, alkoxy, alkyl, haloalkyl, cycloalkyl, and nitrile; wherein $R_5$ and $R_6$ are not both hydrogen.

In some embodiments of Formulas I-V, $R_5$ is alkyl and $R_6$ is alkyl.

In some embodiments of Formulas I-V, $R_5$ is $C_{1-8}$alkyl and $R_6$ is $C_{1-8}$alkyl.

In some embodiments of Formulas I-V, $R_5$ is $C_{1-4}$alkyl and $R_6$ is $C_{1-4}$alkyl.

In some embodiments of Formulas I-V, X is alkylene optionally interrupted by one or more —O— groups; and $R_2$ is selected from the group consisting of hydrogen, alkyl, and alkoxyalkylenyl.

In some embodiments of Formulas II-V, X is alkylene optionally interrupted by one or more —O— groups; $R_2$ is selected from the group consisting of hydrogen, alkyl, and alkoxyalkylenyl; n is 0 or 1, R is selected from the group consisting of halogen, hydroxyl, alkyl, alkoxy, and haloalkyl.

In some embodiments of Formulas I-V, X is alkylene; $R_2$ is selected from the group consisting of hydrogen, alkyl, and alkoxyalkylenyl.

In some embodiments of Formulas I-V, X is alkylene optionally interrupted by one or more —O— groups; $R_5$ and $R_6$ are independently selected from the group consisting of hydrogen and alkyl; $R_2$ is selected from the group consisting of hydrogen, alkyl, and alkoxyalkylenyl; with the proviso that $R_5$ and $R_6$ are not both hydrogen.

In some embodiments of Formulas I-V, X is alkylene; $R_5$ and $R_6$ are independently selected from the group consisting of hydrogen and alkyl; $R_2$ is selected from the group consisting of hydrogen, alkyl, and alkoxyalkylenyl; with the proviso that $R_5$ and $R_6$ are not both hydrogen.

In some embodiments of Formulas I-V, X is alkylene optionally interrupted by one or more —O— groups; $R_5$ is alkyl; $R_6$ is alkyl; $R_2$ is selected from the group consisting of hydrogen, alkyl, and alkoxyalkylenyl.

In some embodiments of Formulas I-V, X is alkylene; $R_5$ is alkyl; $R_6$ is alkyl; $R_2$ is selected from the group consisting of hydrogen, alkyl, and alkoxyalkylenyl.

In some embodiments of Formulas I-V, the compound is present in the form of a salt. The salt is typically a pharmaceutically acceptable salt. Most commonly the salt is a hydrochloride or dihydrochloride salt.

The disclosure also provides compounds of the following Formulas VI-XII:

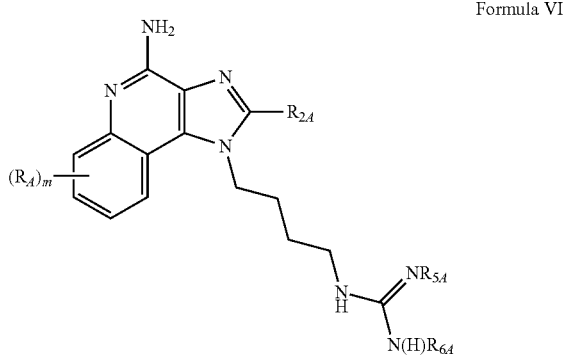

Formula VI

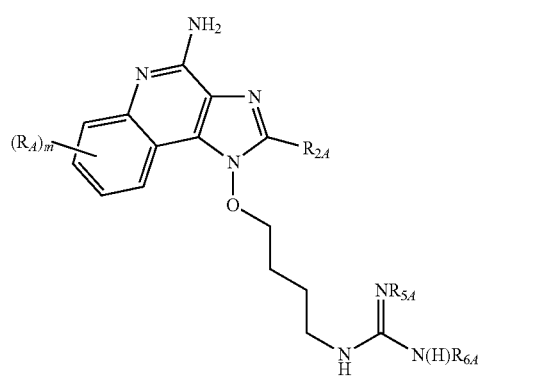

Formula VII

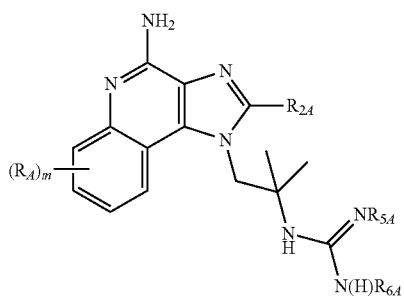

Formula VIII

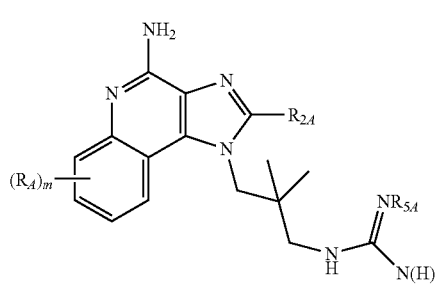

Formula IX

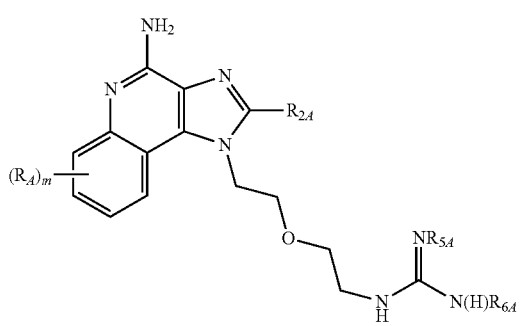

Formula X

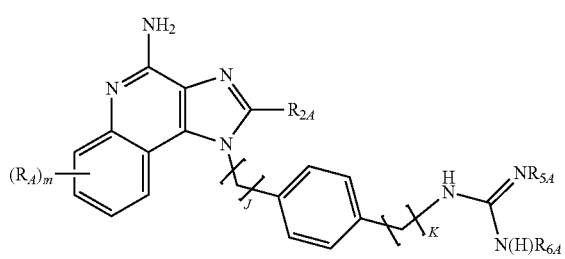

Formula XI

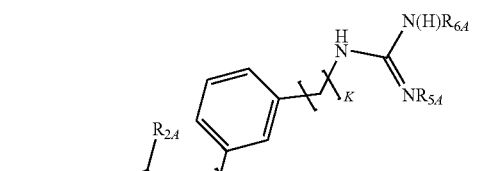

Formula XII wherein $R_A$, $R_{2A}$, $R_{5A}$, $R_{6A}$, m, J, and K are defined for Formulas VI-XII below; and pharmaceutically acceptable salts thereof.

For the compounds of Formulas VI-XII:
m is an integer from 0 to 2;
J is an integer from 1 to 5;
K is an integer from 0 to 7;
$R_A$ is selected from the group consisting of halogen, hydroxyl, alkyl, alkoxy, haloalkyl, —C(O)—O-alkyl, —C(O)—O—CH$_2$Ph, —C(O)—O-aryl, amino, alkylamino, and dialkylamino, aryl, arylalkylenyl, aryloxyalkylenyl, arylalkyleneoxy, aryloxy, heteroaryl, heteroarylalkylenyl, heteroaryloxyalkyenyl, heteroarylalkyleneoxy, and heteroaryloxy, wherein the alkyl, aryl, arylalkylenyl, aryloxyalkylenyl, arylalkyleneoxy, aryloxy, heteroaryl, heteroarylalkylenyl, heteroaryloxyalkyenyl, heteroarylalkyleneoxy, and heteroaryloxy groups can be unsubstituted or substituted by one or more substituents independently selected from the group consisting of alkyl, alkoxy, halogen, haloalkyl, hydroxyl, hydroxyalkylenyl, alkoxyalkylenyl, arylalkyleneoxy, and nitrile;
$R_{2A}$ is selected from the group consisting of hydrogen, alkyl, alkenyl, alkynyl, —O-alkyl, hydroxyalkylenyl, alkoxyalkylenyl, alkylaminoalkylenyl, hydroxyl, —CH$_2$—NH—O-alkyl, and —CH$_2$NHC(O)-alkyl;
$R_{5A}$ and $R_{6A}$ are independently selected from the group consisting of hydrogen, —C(O)—O-alkyl, alkyl, cycloalkyl, aryl, arylalkylenyl, aryloxyalkylenyl, heteroaryl, heteroarylalkylenyl, heteroaryloxyalkylenyl, cycloalkylalkylenyl aryl-(CH$_2$)$_{2-6}$—O-alkylenyl, and benzyloxyalkylenyl; wherein any of the alkyl, cycloalkyl, aryl, arylalkylenyl, aryloxyalkylenyl, heteroaryl, heteroarylalkylenyl, heteroaryloxyalkylenyl, cycloalkylalkylenyl, aryl-(CH$_2$)$_{2-6}$—O-alkylenyl, and benzyloxyalkylenyl groups can be either unsubstituted or substituted with one or more substituents independently selected from the group consisting of halogen, hydroxyl, alkoxy, alkyl, haloalkyl, cycloalkyl, nitrile, aryl, heteroaryl, and dialkylamino; with the proviso that $R_{5A}$ and $R_{6A}$ are not both hydrogen.

In some embodiments of Formulas VI-XII, m is 0 or 1.
In some embodiments of Formulas VI-XII, m is 0.
In some embodiments of Formulas XI-XII, J is 1 and K is an integer from 0 to 4.
In some embodiments of Formulas XI-XII, K is 1 and J is an integer from 1 to 4.
In some embodiments of Formulas XI-XII, K is 1 and J is 1.
In some embodiments of Formulas VI-XII, $R_A$ is selected from the group consisting of halogen, hydroxyl, alkyl, alkoxy, haloalkyl, —C(O)—O-alkyl, —C(O)—OCH$_2$Ph, —C(O)—O-aryl, amino, alkylamino, and dialkylamino.
In some embodiments of Formulas VI-XII, $R_{2A}$ is selected from the group consisting hydrogen, alkyl, alkoxyalkylenyl, alkylaminoalkylenyl, and hydroxyalkylenyl.
In some embodiments of Formulas VI-XII, $R_{2A}$ is selected from the group consisting hydrogen, alkyl, and alkoxyalkylenyl.
In some embodiments of Formulas VI-XII, $R_{2A}$ is selected from the group consisting of hydrogen, —CH$_3$, —CH$_2$CH$_3$, —CH$_2$CH$_2$CH$_3$, —CH$_2$CH$_2$CH$_2$CH$_3$, —CH$_2$OCH$_3$, —CH$_2$OCH$_2$CH$_3$, —CH$_2$CH$_2$OCH$_3$, —CH$_2$NHCH$_3$, —CH$_2$NHCH$_2$CH$_3$, —CH$_2$CH$_2$NHCH$_3$, —CH$_2$OH, —CH$_2$CH$_2$OH, and —CH$_2$NHOCH$_3$.
In some embodiments of Formulas VI-XII, $R_{2A}$ is selected from the group consisting of hydrogen, —CH$_3$, —CH$_2$CH$_3$, —CH$_2$CH$_2$CH$_3$, —CH$_2$CH$_2$CH$_2$CH$_3$, —CH$_2$OCH$_3$, —CH$_2$OCH$_2$CH$_3$, and —CH$_2$CH$_2$OCH$_3$.

In some embodiments of Formulas VI-XII, $R_{2A}$ is —$CH_2NHC(O)CH_3$ or —$CH_2NHC(O)$cyclopropyl.

In some embodiments of Formulas VI-XII, $R_{2A}$ is —$CH_2NHC(O)C_{1-3}$alkyl.

In some embodiments of Formulas VI-XII, $R_{5A}$ and $R_{6A}$ are independently selected from the group consisting of hydrogen, alkyl, cycloalkyl, aryl, arylalkylenyl, aryloxyalkylenyl, heteroaryl, heteroarylalkylenyl, heteroaryloxyalkylenyl, cycloalkylalkylenyl aryl-$(CH_2)_{2-6}$—O-alkylenyl, and benzyloxyalkylenyl; wherein any of the alkyl, cycloalkyl, aryl, arylalkylenyl, aryloxyalkylenyl, heteroaryl, heteroarylalkylenyl, heteroaryloxyalkylenyl, cycloalkylalkylenyl, aryl-$(CH_2)_{2-6}$—O-alkylenyl, and benzyloxyalkylenyl groups can be either unsubstituted or substituted with one or more substituents independently selected from the group consisting of halogen, hydroxyl, alkoxy, alkyl, haloalkyl, cycloalkyl, nitrile, aryl, heteroaryl, and dialkylamino; with the proviso that $R_{5A}$ and $R_{6A}$ are not both hydrogen.

In some embodiments of Formulas VI-XII, $R_{5A}$ and $R_{6A}$ are independently selected from the group consisting of alkyl, cycloalkyl, aryl, arylalkylenyl, aryloxyalkylenyl, heteroaryl, heteroarylalkylenyl, heteroaryloxyalkylenyl, cycloalkylalkylenyl, aryl-$(CH_2)_{2-6}$—O-alkylenyl, and benzyloxyalkylenyl; wherein any of the alkyl, cycloalkyl, aryl, arylalkylenyl, aryloxyalkylenyl, heteroaryl, heteroarylalkylenyl, heteroaryloxyalkylenyl, cycloalkylalkylenyl, aryl-$(CH_2)_{2-6}$—O-alkylenyl, and benzyloxyalkylenyl groups can be either unsubstituted or substituted with one or more substituents independently selected from the group consisting of halogen, hydroxyl, alkoxy, alkyl, haloalkyl, cycloalkyl, nitrile, aryl, heteroaryl, and dialkylamino.

In some embodiments of Formulas VI-XII, $R_{5A}$ and $R_{6A}$ are independently selected from the group consisting of hydrogen, alkyl, phenyl, and phenylalkylenyl; wherein $R_{5A}$ and $R_{6A}$ are not both hydrogen.

In some embodiments of Formulas VI-XII, $R_{5A}$ and $R_{6A}$ are independently selected from the group consisting of hydrogen, alkyl, cycloalkyl, cycloalkylalkylenyl, aryl, and arylalkylenyl; wherein $R_{5A}$ and $R_{6A}$ are not both hydrogen.

In some embodiments of Formulas VI-XII, $R_{5A}$ and $R_{6A}$ are independently selected from the group consisting of hydrogen, —$CH_3$, —$CH_2CH_3$, —$CH(CH_3)_2$, —$CH_2CH_2CH_3$, —$CH_2CH_2CH_2CH_3$, —$CH_2CH(CH_3)_2$, —$C(CH_3)_3$, —$CH_2CH_2CH_2CH_2CH_3$, —$(CH_2)_{5-9}CH_3$, —$CH_2CH_2CH(CH_3)_2$, cyclopropyl, cyclopentyl, cyclohexyl, —$CH_2$-cyclopropyl, —$CH_2$-cyclopentyl, —$CH_2$-cyclohexyl, —$CH_2CH_2OCH_3$, —$(CH_2)_{3-8}$—O—$CH_3$, and —$CH_2CH_2CH_2N(CH_3)_2$; wherein $R_{5A}$ and $R_{6A}$ are not both hydrogen.

In some embodiments of Formulas VI-XII, $R_{5A}$ and $R_{6A}$ are independently selected from the group consisting of hydrogen, alkyl, —$CH_2Ph$, —$CH_2CH_2Ph$, —$CH_2CH_2$—O-Ph, -Ph, —$(CH_2)_{3-8}Ph$, —$(CH_2)_{3-8}$—O-Ph, —$CH_2CH_2$—O—$CH_2Ph$, —$(CH_2)_{3-8}$—O—$CH_2Ph$, and —$(CH_2)_{2-8}$—O—$(CH_2)_{1-4}Ph$, wherein the Ph group can be either unsubstituted or substituted with one or more substituents independently selected from the group consisting of halogen, hydroxyl, alkoxy, alkyl, haloalkyl, cycloalkyl, and nitrile; and wherein $R_{5A}$ and $R_{6A}$ are not both hydrogen.

In some embodiments of Formulas VI-XII, $R_{5A}$ is alkyl and $R_{6A}$ is alkyl.

In some embodiments of Formulas VI-XII, $R_{5A}$ is $C_{1-8}$alkyl and $R_{6A}$ is $C_{1-8}$alkyl.

In some embodiments of Formulas VI-XII, $R_{5A}$ is $C_{1-4}$alkyl and $R_{6A}$ is $C_{1-4}$alkyl.

In some embodiments of Formulas VI-XII, the compound is present in the form of a salt. The salt is typically a pharmaceutically acceptable salt. Most commonly the salt is a hydrochloride or dihydrochloride salt.

This disclosure also provides compounds of the following Formula XIII:

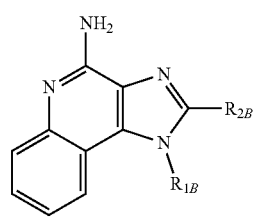

Formula XIII wherein $R_{1B}$, and $R_{2B}$, and are as defined below; as well as salts thereof, which are typically pharmaceutically acceptable salts.

For compounds and salts, such as pharmaceutically acceptable salts, of Formula XIII: $R_{1B}$ is selected from the group consisting of —$X_B$—N($R_{7B}$)—C(=N—$R_{5B}$)—N(H)$R_{6B}$, —$Z_B$—N($R_{7B}$)—C(=N—$R_{5B}$)—N(H)$R_{6B}$, and

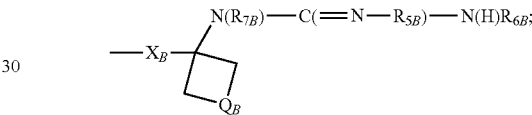

$X_B$ is selected from the group consisting of alkylene, alkenylene, and alkynylene, wherein the alkylene, alkenylene, and alkynylene groups can be optionally interrupted by one or more —O— groups;

$Z_B$ is selected from the group consisting of
—$X_B$-arylene-$X_B$—,
—$X_B$-heteroarylene-$X_B$—,
—$X_B$-arylene-, and
—$X_B$-heteroarylene-;

$R_{2B}$ is selected from the group consisting of hydrogen, alkyl, alkenyl, alkynyl, —O-alkyl, hydroxyalkylenyl, alkoxyalkylenyl, alkylaminoalkylenyl, hydroxyl, —$CH_2$—NH—O-alkyl, and —$CH_2NHC(O)$-alkyl;

$R_{7B}$ is selected from the group consisting of hydrogen, alkyl, arylalkylenyl, alkoxyalkylenyl, aryloxyalkylenyl, benzyloxyalkylenyl, aryl-$(CH_2)_{2-6}$—O-alkylenyl, and cycloalkylalkylenyl; wherein any of the alkyl, arylalkylenyl, alkoxyalkylenyl, aryloxyalkylenyl, benzyloxyalkylenyl, aryl-$(CH_2)_{2-6}$—O-alkylenyl, and cycloalkylalkylenyl groups can be either unsubstituted or substituted with one or more substituents selected from the group consisting of halogen, hydroxyl, alkyl, alkoxy, haloalkyl, and nitrile;

Q is selected from the group consisting of a covalent bond, —$CH_2$—, —$CH_2CH_2$—, —$CH_2CH_2CH_2$—, —$CH_2CH_2CH_2CH_2$—, —$CH_2CH_2CH_2CH_2CH_2$—, —$CH_2$—O—$CH_2$—, and —$OCH_2$—;

$R_{5B}$ and $R_{6B}$ are independently selected from the group consisting of hydrogen, —C(O)—O-alkyl, alkyl, cycloalkyl, aryl, arylalkylenyl, aryloxyalkylenyl, heteroaryl, heteroarylalkylenyl, heteroaryloxyalkylenyl, cycloalkylalkylenyl, aryl-$(CH_2)_{2-6}$—O-alkylenyl, and benzyloxyalkylenyl; wherein any of the alkyl, cycloalkyl, aryl, arylalkylenyl, aryloxyalkylenyl, heteroaryl, heteroarylalkylenyl, heteroaryloxyalkylenyl, cycloalkylalkylenyl, aryl-$(CH_2)_{2-6}$—

O-alkylenyl, and benzyloxyalkylenyl groups can be either unsubstituted or substituted with one or more substituents independently selected from the group consisting of halogen, hydroxyl, alkoxy, alkyl, haloalkyl, cycloalkyl, nitrile, aryl, heteroaryl, and dialkylamino; with the proviso that $R_{5B}$ and $R_{6B}$ are not both hydrogen.

In some embodiments of Formula XIII, $R_{2B}$ is selected from the group consisting hydrogen, alkyl, alkoxyalkylenyl, alkylaminoalkylenyl, and hydroxyalkylenyl.

In some embodiments of Formula XIII, $R_{2B}$ is selected from the group consisting hydrogen, alkyl, and alkoxyalkylenyl.

In some embodiments of Formula XIII, $R_{2B}$ is selected from the group consisting of hydrogen, —$CH_3$, —$CH_2CH_3$, —$CH_2CH_2CH_3$, —$CH_2CH_2CH_2CH_3$, —$CH_2OCH_3$, —$CH_2OCH_2CH_3$, —$CH_2CH_2OCH_3$, —$CH_2NHCH_3$, —$CH_2NHCH_2CH_3$, —$CH_2CH_2NHCH_3$, —$CH_2OH$, —$CH_2CH_2OH$, and —$CH_2NHOCH_3$.

In some embodiments of Formula XIII, $R_{2B}$ is selected from the group consisting of hydrogen, —$CH_3$, —$CH_2CH_3$, —$CH_2CH_2CH_3$, —$CH_2CH_2CH_2CH_3$, —$CH_2OCH_3$, —$CH_2OCH_2CH_3$, and —$CH_2CH_2OCH_3$.

In some embodiments of Formula XIII, $R_{2B}$ is —$CH_2NHC(O)CH_3$ or —$CH_2NHC(O)$cyclopropyl.

In some embodiments of Formula XIII, $R_{2B}$ is —$CH_2NHC(O)C_{1-3}$alkyl.

In some embodiments of Formula XIII, $R_{7B}$ is hydrogen, $C_{1-8}$alkyl, or —$CH_2Ph$.

In some embodiments of Formula XIII, $R_{7B}$ is hydrogen or $C_{1-4}$alkyl.

In some embodiments of Formula XIII, $R_{7B}$ is hydrogen.

In some embodiments of Formula XIII, $R_{7B}$ is selected from the group consisting of hydrogen, —$CH_3$, —$CH_2CH_3$, —$CH(CH_3)_2$, —$CH_2CH_2CH_3$, —$CH_2CH_2CH_2CH_3$, —$CH_2CH(CH_3)_2$, —$C(CH_3)_3$, —$CH_2CH_2CH_2CH_2CH_3$, —$CH_2CH_2CH(CH_3)_2$, cyclopentyl, -cyclohexyl, —$CH_2$(cyclopentyl), —$CH_2$(cyclohexyl), and —$CH_2CH_2$—O—$CH_3$.

In some embodiments of Formula XIII, $R_{7B}$ is selected from the group consisting of hydrogen, alkyl, —$CH_2Ph$, —$CH_2CH_2Ph$, —$CH_2CH_2$—O-Ph, —$CH_2CH_2$—O—$CH_2Ph$, and —$(CH_2)_{2-6}$—O—$(CH_2)_{1-6}Ph$, wherein Ph can be either unsubstituted or substituted with one or more substituents selected from the group consisting of halogen, hydroxyl, alkyl, alkoxy, haloalkyl, and nitrile.

In some embodiments of Formula XIII, $R_{5B}$ and $R_{6B}$ are independently selected from the group consisting of hydrogen, alkyl, cycloalkyl, aryl, arylalkylenyl, aryloxyalkylenyl, heteroaryl, heteroarylalkylenyl, heteroaryloxyalkylenyl, cycloalkylalkylenyl aryl-$(CH_2)_{2-6}$—O-alkylenyl, and benzyloxyalkylenyl; wherein any of the alkyl, cycloalkyl, aryl, arylalkylenyl, aryloxyalkylenyl, heteroaryl, heteroarylalkylenyl, heteroaryloxyalkylenyl, cycloalkylalkylenyl, aryl-$(CH_2)_{2-6}$—O-alkylenyl, and benzyloxyalkylenyl groups can be either unsubstituted or substituted with one or more substituents independently selected from the group consisting of halogen, hydroxyl, alkoxy, alkyl, haloalkyl, cycloalkyl, nitrile, aryl, heteroaryl, and dialkylamino; with the proviso that $R_{5A}$ and $R_{6A}$ are not both hydrogen.

In some embodiments of Formula XIII, $R_{5B}$ and $R_{6B}$ are independently selected from the group consisting of alkyl, cycloalkyl, aryl, arylalkylenyl, aryloxyalkylenyl, heteroaryl, heteroarylalkylenyl, heteroaryloxyalkylenyl, cycloalkylalkylenyl, aryl-$(CH_2)_{2-6}$—O-alkylenyl, and benzyloxyalkylenyl; wherein any of the alkyl, cycloalkyl, aryl, arylalkylenyl, aryloxyalkylenyl, heteroaryl, heteroarylalkylenyl, heteroaryloxyalkylenyl, cycloalkylalkylenyl, aryl-$(CH_2)_{2-6}$—O-alkylenyl, and benzyloxyalkylenyl groups can be either unsubstituted or substituted with one or more substituents independently selected from the group consisting of halogen, hydroxyl, alkoxy, alkyl, haloalkyl, cycloalkyl, nitrile, aryl, heteroaryl, and dialkylamino.

In some embodiments of Formula XIII, $R_{5B}$ and $R_{6B}$ are independently selected from the group consisting of hydrogen, alkyl, phenyl, and phenylalkylenyl; wherein $R_{5B}$ and $R_{6B}$ are not both hydrogen.

In some embodiments of Formula XIII, $R_{5B}$ and $R_{6B}$ are independently selected from the group consisting of hydrogen, alkyl, cycloalkyl, cycloalkylalkylenyl, aryl, and arylalkylenyl; wherein $R_{5B}$ and $R_{6B}$ are not both hydrogen.

In some embodiments of Formula XIII, $R_{5B}$ and $R_{6B}$ are independently selected from the group consisting of hydrogen, —$CH_3$, —$CH_2CH_3$, —$CH(CH_3)_2$, —$CH_2CH_2CH_3$, —$CH_2CH_2CH_2CH_3$, —$CH_2CH(CH_3)_2$, —$C(CH_3)_3$, —$CH_2CH_2CH_2CH_2CH_3$, —$(CH_2)_{5-9}CH_3$, —$CH_2CH_2CH(CH_3)_2$, cyclopropyl, cyclopentyl, cyclohexyl, —$CH_2$-cyclopropyl, —$CH_2$-cyclopentyl, —$CH_2$-cyclohexyl, —$(CH_2)_{3-8}$—O—$CH_3$, —$CH_2CH_2OCH_3$, and —$CH_2CH_2CH_2N(CH_3)_2$; and wherein $R_{5B}$ and $R_{6B}$ are not both hydrogen.

In some embodiments of Formula XIII, $R_{5B}$ and $R_{6B}$ are independently selected from the group consisting of hydrogen, alkyl, —$CH_2Ph$, —$CH_2CH_2Ph$, —$CH_2CH_2$—O-Ph, -Ph, —$(CH_2)_{3-8}Ph$, —$(CH_2)_{3-8}$—O-Ph, —$CH_2CH_2$—O—$CH_2Ph$, —$(CH_2)_{3-8}$—O—$CH_2Ph$, and —$(CH_2)_{2-8}$—O—$(CH_2)_{1-4}Ph$, wherein the Ph group can be either unsubstituted or substituted with one or more substituents independently selected from the group consisting of halogen, hydroxyl, alkoxy, alkyl, haloalkyl, cycloalkyl, and nitrile, with the proviso that $R_{5B}$ and $R_{6B}$ are not both hydrogen.

In some embodiments of Formula XIII, $R_{5B}$ is alkyl and $R_{6B}$ is alkyl.

In some embodiments of Formula XIII, $R_{5B}$ is $C_{1-8}$alkyl and $R_{6B}$ is $C_{1-8}$alkyl.

In some embodiments of Formula XIII, $R_{5B}$ is $C_{1-4}$alkyl and $R_{6B}$ is $C_{1-4}$alkyl.

In some embodiments of Formula XIII, $X_B$ is alkylene optionally interrupted by one or more —O— groups.

In some embodiments of Formula XIII, $X_B$ is a $C_{2-12}$alkylene optionally interrupted by one or more —O— groups.

In some embodiments of Formula XIII, $X_B$ is a $C_{2-8}$alkylene optionally interrupted by one or more —O— groups.

In some embodiments of Formula XIII, $X_B$ is $C_{2-8}$alkylene.

In some embodiments of Formula XIII, $X_B$ is $C_{2-6}$alkylene.

In some embodiments of Formula XIII, $X_B$ is $C_{2-8}$alkylene.

In some embodiments of Formula XIII, $X_B$ is selected from the group consisting of —$CH_2CH_2$—, —$CH_2CH_2CH_2$—, —$CH_2CH_2CH_2CH_2$—, —$CH_2CH_2CH_2CH_2CH_2$—, —$CH_2CH_2CH_2CH_2CH_2CH_2$—, —$CH_2CH_2CH_2CH_2CH_2CH_2CH_2$—, —$CH_2CH_2CH_2CH_2CH_2CH_2CH_2CH_2$—, —$CH_2C(CH_3)_2$—, —$CH_2C(CH_3)_2CH_2$—, —$CH_2CH_2$—O—$CH_2CH_2$—, —$CH_2CH_2$—O—$CH_2CH_2$—O—$CH_2CH_2$—, —$(CH_2)_{2-4}$—$(OCH_2CH_2$—$)_{1-5}$, and, —$(CH_2)_{2-6}$—$(OCH_2CH_2$—$)_{1-4}$.

In some embodiments of Formula XIII, $Z_B$ is —$C_{1-5}$alkylene-arylene-$C_{1-5}$alkylene- or —$C_{1-5}$alkylene-heteroarylene-$C_{1-5}$alkylene-.

In some embodiments of Formula XIII, $Z_B$ is —$CH_2$-phenylene-$CH_2$—.

In some embodiments of Formula XIII, $R_{1B}$ is —$X_B$—N(H)—C(=N—$R_{5B}$)—N(H)$R_{6B}$, and —$Z_B$—N(H)—C(=N—$R_{5B}$)—N(H)$R_{6B}$; In some embodiments of Formula XIII, $R_{1B}$ is —$X_B$—N(H)—C(=N—$R_{5B}$)—N(H)$R_{6B}$.

In some embodiments of Formula XIII, $X_B$ is alkylene optionally interrupted by one or more —O— groups; $R_{2B}$ is selected from the group consisting of hydrogen, alkyl, and alkoxyalkylenyl.

In some embodiments of Formula XIII, $X_B$ is alkylene; $R_{2B}$ is selected from the group consisting of hydrogen, alkyl, and alkoxyalkylenyl.

In some embodiments of Formula XIII, $X_B$ is alkylene optionally interrupted by one or more —O— groups; $R_{5B}$ and $R_{6B}$ are independently selected from the group consisting of hydrogen and alkyl; $R_{2B}$ is selected from the group consisting of hydrogen, alkyl, and alkoxyalkylenyl; with the proviso that $R_{5B}$ and $R_{6B}$ are not both hydrogen.

In some embodiments of Formula XIII, $X_B$ is alkylene; $R_{5B}$ and $R_{6B}$ are independently selected from the group consisting of hydrogen and alkyl; $R_{2B}$ is selected from the group consisting of hydrogen, alkyl, and alkoxyalkylenyl; with the proviso that $R_{5B}$ and $R_{6B}$ are not both hydrogen.

In some embodiments of Formula XIII, $X_B$ is alkylene optionally interrupted by one or more —O— groups; $R_{5B}$ is alkyl; $R_{6B}$ is alkyl; $R_{2B}$ is selected from the group consisting of hydrogen, alkyl, and alkoxyalkylenyl.

In some embodiments of Formula XIII, $X_B$ is alkylene; $R_{5B}$ is alkyl; $R_{6B}$ is alkyl; $R_{2B}$ is selected from the group consisting of hydrogen, alkyl, and alkoxyalkylenyl.

In some embodiments of Formula XIII, the compound is present in the form of a salt. The salt is typically a pharmaceutically acceptable salt. Most commonly the salt is a hydrochloride or dihydrochloride salt.

The disclosure provides a method of inducing cytokine biosynthesis in an animal comprising administering to the animal an effective amount of a compound or salt selected from the group consisting of any one of the above embodiments of Formulas I-XIII.

The disclosure provides a method of inducing IFN-alpha biosynthesis in an animal by administering to the animal an effective amount of a compound or salt selected from any one of the above embodiments of Formulas I-XIII.

The disclosure provides a method of inducing IFN-gamma biosynthesis in an animal by administering to the animal an effective amount of a compound or salt selected from any one of the above embodiments of Formulas I-XIII.

The disclosure provides a method of inducing TNF-alpha biosynthesis in an animal by administering to the animal an effective amount of a compound or salt selected from any one of the above embodiments of Formulas I-XIII.

The disclosure provides a method of inducing IP-10 biosynthesis in an animal by administering to the animal an effective amount of a compound or salt selected from any one of the above embodiments of Formulas I-XIII.

The disclosure also provides a method of treating a viral disease in an animal by administering to the animal an effective amount of a compound or salt selected from any one of the above embodiments of Formulas I-XIII.

The disclosure also provides a method of treating a neoplastic disease in an animal by administering to the animal an effective amount of a compound or salt selected from any one of the above embodiments of Formulas I-XIII.

This disclosure also provides compounds of the following Formula XIV:

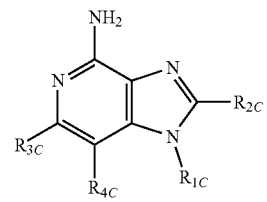

Formula XIV wherein $R_{1C}$, $R_{2C}$, $R_{3C}$, and $R_{4C}$ are as defined below; and pharmaceutically acceptable salts thereof.

Examples of compounds of Formula XIV are more specifically defined by the following Formulas XV-XVIII:

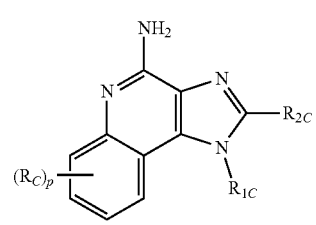

Formula XV

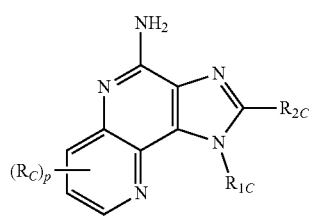

Formula XVI

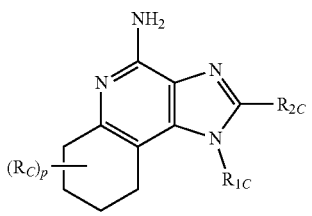

Formula XVII

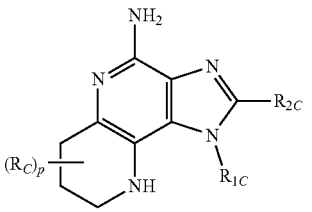

Formula XVIII wherein $R_C$, $R_{1C}$, $R_{2C}$, and p are as defined below; and pharmaceutically acceptable salts thereof.

For compounds and salts, such as pharmaceutically acceptable salts, of Formula XIV, $R_{3C}$ and $R_{4C}$ are taken together to form a fused benzene ring, a fused pyridine ring, a fused cyclohexene ring, or a fused tetrahydropyridine ring; wherein the fused benzene ring, fused pyridine ring, fused cyclohexene ring, or fused tetrahydropyridine ring is either unsubstituted or substituted by one or more $R_C$ groups.

For compounds and salts, such as pharmaceutically acceptable salts, of Formulas XIV-XVIII:
$R_C$ is selected from the group consisting of halogen, hydroxyl, alkyl, alkoxy, haloalkyl, —C(O)—O-alkyl, —C(O)—O—CH$_2$Ph, —C(O)—O-aryl, amino, alkylamino, and dialkylamino, aryl, arylalkylenyl, aryloxyalkylenyl, arylalkyleneoxy, aryloxy, heteroaryl, heteroarylalkylenyl, heteroaryloxyalkyenyl, heteroarylalkyleneoxy, and heteroaryloxy, wherein the alkyl, aryl, arylalkylenyl, aryloxyalkylenyl, arylalkyleneoxy, aryloxy, heteroaryl, heteroarylalkylenyl, heteroaryloxyalkyenyl, heteroarylalkyleneoxy, and heteroaryloxy groups can be unsubstituted or substituted by one or more substituents independently selected from the group consisting of alkyl, alkoxy, halogen, haloalkyl, hydroxyl, hydroxyalkylenyl, alkoxyalkylenyl, arylalkyleneoxy, and nitrile;

p is an integer from 0 to 2;

$R_{1C}$ is selected from the group consisting of

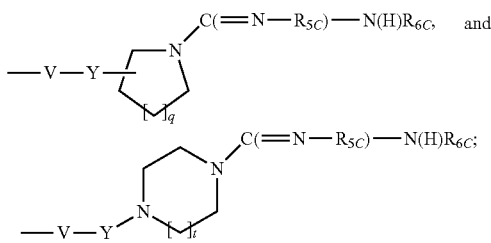

V is selected from the group consisting of a covalent bond, —O—, and —NH—;

Y is selected from the group consisting of alkylene, alkenylene, and alkynylene, wherein any of the alkylene, alkenylene, and alkynylene can be optionally interrupted by one or more —O— groups;

$R_{2C}$ is selected from the group consisting of hydrogen, alkyl, alkenyl, alkynyl, —O-alkyl, hydroxyalkylenyl, alkoxyalkylenyl, alkylaminoalkylenyl, hydroxyl, —CH$_2$—NH—O-alkyl, and —CH$_2$NHC(O)-alkyl;

$R_{5C}$ and $R_{6C}$ are independently selected from the group consisting of hydrogen, —C(O)—O-alkyl, alkyl, cycloalkyl, aryl, arylalkylenyl, aryloxyalkylenyl, heteroaryl, heteroarylalkylenyl, heteroaryloxyalkylenyl, cycloalkylalkylenyl, aryl-(CH$_2$)$_{2-6}$—O-alkylenyl, and benzyloxyalkylenyl; wherein any of the alkyl, cycloalkyl, aryl, arylalkylenyl, aryloxyalkylenyl, heteroaryl, heteroarylalkylenyl, heteroaryloxyalkylenyl, cycloalkylalkylenyl, aryl-(CH$_2$)$_{2-6}$—O-alkylenyl, and benzyloxyalkylenyl groups can be either unsubstituted or substituted with one or more substituents independently selected from the group consisting of halogen, hydroxyl, alkoxy, alkyl, haloalkyl, cycloalkyl, nitrile, aryl, heteroaryl, and dialkylamino, with the proviso that $R_{5C}$ and $R_{6C}$ are not both hydrogen.

q is an integer from 0 to 5;

t is an integer from 1 to 4.

In some embodiments of Formula XIV, $R_{3C}$ and $R_{4C}$ are taken together to form a fused benzene ring, a fused pyridine ring, or a fused cyclohexene ring.

In some embodiments of Formula XIV, $R_{3C}$ and $R_{4C}$ are taken together to form a fused benzene ring or a fused cyclohexene ring.

In some embodiments of Formula XIV, $R_{3C}$ and $R_{4C}$ are taken together to form a fused benzene ring or a fused pyridine ring.

In some embodiments of Formula XIV, $R_{3C}$ and $R_{4C}$ are taken together to form a fused benzene ring.

In some embodiments of Formula XIV, $R_{3C}$ and $R_{4C}$ are taken together to form a fused benzene ring, a fused pyridine ring, or a fused cyclohexene ring; wherein the fused benzene ring, fused pyridine ring, or fused cyclohexene ring is either unsubstituted or substituted by one $R_C$ group.

In some embodiments of Formula XIV, $R_{3C}$ and $R_{4C}$ are taken together to form a fused benzene ring or a fused pyridine ring; wherein the fused benzene ring or fused pyridine ring is either unsubstituted or substituted by one $R_C$ group.

In some embodiments of Formulas XV-XVIII, p is 0 or 1.

In some embodiments of Formulas XV-XVIII, p is 0.

In some embodiments of Formulas XV-XVIII, $R_C$ is selected from the group consisting of halogen, hydroxyl, alkyl, alkoxy, haloalkyl, —C(O)—O-alkyl, —C(O)—OCH$_2$Ph, —C(O)—O-aryl, amino, alkylamino, and dialkylamino.

In some embodiments of Formulas XIV-XVIII, V is a covalent bond and Y is alkylene optionally interrupted by one or more —O— groups.

In some embodiments of Formulas XIV-XVIII, —V—Y— is —O—C$_{1-7}$alkylene- or —C$_{1-8}$alkylene-.

In some embodiments of Formulas XIV-XIII, —V—Y— is —CH$_2$—, —CH$_2$CH$_2$—, —CH$_2$CH$_2$CH$_2$—, —CH$_2$CH$_2$CH$_2$CH$_2$—, —CH$_2$CH$_2$CH$_2$CH$_2$CH$_2$—, —CH$_2$CH$_2$CH$_2$CH$_2$CH$_2$CH$_2$—, or —CH$_2$CH$_2$—O—CH$_2$CH$_2$—.

In some embodiments of Formulas XIV-XVIII, $R_{2C}$ is selected from the group consisting hydrogen, alkyl, alkoxyalkylenyl, alkylaminoalkylenyl, and hydroxyalkylenyl.

In some embodiments of Formulas XIV-XVIII, $R_{2C}$ is selected from the group consisting hydrogen, alkyl, and alkoxyalkylenyl.

In some embodiments of Formulas XIV-XVIII, $R_{2C}$ is selected from the group consisting of hydrogen, —CH$_3$, —CH$_2$CH$_3$, —CH$_2$CH$_2$CH$_3$, —CH$_2$CH$_2$CH$_2$CH$_3$, —CH$_2$OCH$_3$, —CH$_2$OCH$_2$CH$_3$, —CH$_2$CH$_2$OCH$_3$, —CH$_2$NHCH$_3$, —CH$_2$NHCH$_2$CH$_3$, —CH$_2$CH$_2$NHCH$_3$, —CH$_2$OH, —CH$_2$CH$_2$OH, and —CH$_2$NHOCH$_3$.

In some embodiments of Formulas XIV-XVIII, $R_{2C}$ is selected from the group consisting of hydrogen, —CH$_3$, —CH$_2$CH$_3$, —CH$_2$CH$_2$CH$_3$, —CH$_2$CH$_2$CH$_2$CH$_3$, —CH$_2$OCH$_3$, —CH$_2$OCH$_2$CH$_3$, and —CH$_2$CH$_2$OCH$_3$.

In some embodiments of Formulas XIV-XVIII, q is an integer from 1 to 4.

In some embodiments of Formulas XIV-XVIII, q is 2.

In some embodiments of Formulas XIV-XVIII, t is 1.

In some embodiments of Formulas XIV-XVIII, $R_{5C}$ and $R_{6C}$ are independently selected from the group consisting of hydrogen, alkyl, cycloalkyl, aryl, arylalkylenyl, aryloxyalkylenyl, heteroaryl, heteroarylalkylenyl, heteroaryloxyalkylenyl, cycloalkylalkylenyl aryl-(CH$_2$)$_{2-6}$—O-alkylenyl, and benzyloxyalkylenyl; wherein any of the alkyl, cycloalkyl, aryl, arylalkylenyl, aryloxyalkylenyl, heteroaryl, heteroarylalkylenyl, heteroaryloxyalkylenyl, cycloalkylalkylenyl, aryl-(CH$_2$)$_{2-6}$—O-alkylenyl, and benzyloxyalkylenyl groups can be either unsubstituted or substituted with one or more substituents independently selected from the group consisting of halogen, hydroxyl, alkoxy, alkyl, haloalkyl, cycloalkyl, nitrile, aryl, heteroaryl, and dialkylamino; with the proviso that $R_{5A}$ and $R_{6A}$ are not both hydrogen.

In some embodiments of Formulas XIV-XVIII, $R_{5C}$ and $R_{6C}$ are independently selected from the group consisting of alkyl, cycloalkyl, aryl, arylalkylenyl, aryloxyalkylenyl, heteroaryl, heteroarylalkylenyl, heteroaryloxyalkylenyl, cycloalkylalkylenyl, aryl-(CH$_2$)$_{2-6}$—O-alkylenyl, and benzyloxyalkylenyl; wherein any of the alkyl, cycloalkyl, aryl, arylalkylenyl, aryloxyalkylenyl, heteroaryl, heteroarylalkylenyl, heteroaryloxyalkylenyl, cycloalkylalkylenyl, aryl- $(CH_2)_{2-6}$—O-alkylenyl, and benzyloxyalkylenyl groups can be either unsubstituted or substituted with one or more substituents independently selected from the group consisting of halogen, hydroxyl, alkoxy, alkyl, haloalkyl, cycloalkyl, nitrile, aryl, heteroaryl, and dialkylamino.

In some embodiments of Formulas XIV-XVIII, $R_{5C}$ and $R_{6C}$ are independently selected from the group consisting of hydrogen, alkyl, phenyl, and phenylalkylenyl; wherein $R_{5C}$ and $R_{6C}$ are not both hydrogen.

In some embodiments of Formulas XIV-XVIII, $R_{5C}$ and $R_{6C}$ are independently selected from the group consisting of hydrogen and $C_{1-8}$alkyl; wherein $R_{5C}$ and $R_{6C}$ are not both hydrogen.

In some embodiments of Formulas XIV-XVIII, $R_{5C}$ and $R_{6C}$ are independently selected from the group consisting of hydrogen, —$CH_3$, —$CH_2CH_3$, —$CH(CH_3)_2$, —$CH_2CH_2CH_3$, —$CH_2CH_2CH_2CH_3$, —$CH_2CH(CH_3)_2$, —$C(CH_3)_3$, —$CH_2CH_2CH_2CH_2CH_3$, —$(CH_2)_{5-9}CH_3$, —$CH_2CH_2CH(CH_3)_2$, cyclopropyl, cyclopentyl, cyclohexyl, —$CH_2$-cyclopropyl, —$CH_2$-cyclopentyl, —$CH_2$-cyclohexyl, —$(CH_2)_{3-8}$—O—$CH_3$, —$CH_2CH_2OCH_3$, and —$CH_2CH_2CH_2N(CH_3)_2$; wherein $R_{5C}$ and $R_{6C}$ are not both hydrogen.

In some embodiments of Formulas XIV-XVIII, $R_{5C}$ and $R_{6C}$ are independently selected from the group consisting of hydrogen, alkyl, —$CH_2Ph$, —$CH_2CH_2Ph$, —$CH_2CH_2$—O—Ph, -Ph, —$(CH_2)_{3-8}Ph$, —$(CH_2)_{3-8}$—O-Ph, —$CH_2CH_2$—O—$CH_2Ph$, —$(CH_2)_{3-8}$—O—$CH_2Ph$, and —$(CH_2)_{2-8}$—O—$(CH_2)_{1-4}Ph$, wherein the Ph group can be substituted with one or more substituents selected from the group consisting of fluorine, chlorine, bromine, hydroxyl, alkyl, alkoxy, and nitrile; wherein $R_{5C}$ and $R_{6C}$ are not both hydrogen.

In some embodiments of Formulas XIV-XVIII, $R_{5C}$ and $R_{6C}$ are independently selected from the group consisting of hydrogen, alkyl, cycloalkyl, cycloalkylalkylenyl, aryl, and arylalkylenyl; wherein $R_{5C}$ and $R_{6C}$ are not both hydrogen.

In some embodiments of Formulas XIV-XVIII, $R_{5C}$ and $R_{6C}$ are independently selected from the group consisting of hydrogen, alkyl, phenyl, and phenylalkylenyl; wherein $R_{5C}$ and $R_{6C}$ are not both hydrogen.

In some embodiments of Formulas XIV-XVIII, $R_{5C}$ is alkyl and $R_{6C}$ is alkyl.

In some embodiments of Formulas XIV-XVIII, $R_{5C}$ is $C_{1-8}$alkyl and $R_{6C}$ is $C_{1-8}$alkyl.

In some embodiments of Formulas XIV-XVIII, $R_{5C}$ is $C_{1-4}$alkyl and $R_{6C}$ is $C_{1-4}$alkyl.

In some embodiments of Formulas XIV-XVIII, V is selected from the group consisting of a covalent bond and —O—; Y is alkylene optionally interrupted by one or more —O— groups; n is 0; q is an integer from 1 to 2; t is 1; $R_{2C}$ is selected from the group consisting of hydrogen, —$CH_3$, —$CH_2CH_3$, —$CH_2CH_2CH_3$, —$CH_2CH_2CH_2CH_3$, —$CH_2OCH_3$, —$CH_2OCH_2CH_3$, and —$CH_2CH_2OCH_3$; $R_{5C}$ and $R_{6C}$ are independently selected from the group consisting of hydrogen, alkyl, cycloalkyl, cycloalkylalkylenyl, aryl, and arylalkylenyl, with the proviso that $R_{5C}$ and $R_{6C}$ are not both hydrogen.

The disclosure provides a method of inducing cytokine biosynthesis in an animal by administering to the animal an effective amount of a compound or salt selected from the group consisting of any one of the above embodiments of Formula XIV, Formula XV, Formula XVI, Formula XVII, and Formula XVIII.

The disclosure also provides a method of inducing cytokine biosynthesis in an animal by administering to the animal an effective amount of a compound or salt selected from the group consisting of any one of the above embodiments of Formula XIV, Formula XV, Formula XVI, Formula XVII, and Formula XVIII; wherein V is a covalent bond, Y is alkylene optionally interrupted by one or more —O— groups, q is 1 or 2, t is 1, and $R_{2C}$ is selected from the group consisting of hydrogen, alkyl and alkoxyalkylenyl.

The disclosure also provides a method of inducing IFN-alpha biosynthesis in an animal by administering to the animal an effective amount of a compound or salt selected from any one of the above embodiments of Formula XIV, Formula XV, Formula XVI, Formula XVII, or Formula XVIII.

The disclosure also provides a method of inducing IFN-gamma biosynthesis in an animal by administering to the animal an effective amount of a compound or salt selected from any one of the above embodiments of Formula XIV, Formula XV, Formula XVI, Formula XVII, or Formula XVIII.

The disclosure also provides a method of inducing TNF-alpha biosynthesis in an animal by administering to the animal an effective amount of a compound or salt selected from any one of the above embodiments of Formula XIV, Formula XV, Formula XVI, Formula XVII, or Formula XVIII.

The disclosure also provides a method of inducing IP-10 biosynthesis in an animal by administering to the animal an effective amount of a compound or salt selected from any one of the above embodiments of Formula XIV, Formula XV, Formula XVI, Formula XVII, or Formula XVIII.

The disclosure also provides a method for treating a viral disease in an animal by administering to the animal an effective amount of a compound or salt selected from the group consisting of any one of the above embodiments of Formula XIV, Formula XV, Formula XVI, Formula XVII, and Formula XVIII.

The disclosure also provides a method for treating a neoplastic disease in an animal by administering to the animal an effective amount of a compound or salt selected from the group consisting of any one of the above embodiments of Formula XIV, Formula XV, Formula XVI, Formula XVII, and Formula XVIII.

The compounds of the disclosure may be synthesized by synthetic routes that include processes analogous to those well known in the chemical arts, particularly in light of the description contained herein. The starting materials are generally available from commercial sources such as Sigma-Aldrich Company (St. Louis, Mo.) or are readily prepared using methods well known to those of ordinary skill in the art (e.g., prepared by methods generally described in Louis F. Fieser and Mary Fieser, Reagents for Organic Synthesis, v. 1-26, Wiley, New York; Alan R. Katritsky, Otto Meth-Cohn, Charles W. Rees, Comprehensive Organic Functional Group Transformations, v 1-6, Pergamon Press, Oxford, England, (1995); Barry M. Trost and Ian Fleming, Comprehensive Organic Synthesis, v. 1-8, Pergamon Press, Oxford, England, (1991); or Beilsteins Handbuch der Organischen Chemie, 4, Aufl. Ed. Springer-Verlag, Berlin, Germany, including supplements (also available via the Beilstein online database)).

Specifically, the compounds of the disclosure can be prepared using one of several standard methods for preparing guanidine containing compounds. Several standard methods are known to those of ordinary skill in the art for converting amino groups to guanidines (see Katritzky, *ARKIVOC*, 2005, iv, pages 49-87; Zhang, *Chem Commun*, 2015, 51, pages 254-265). For example, amine compounds (such as those of Formulas XIX-XXXI) can be reacted with an activated thiourea to provide the compounds of the disclosure (see Maryanoff, *Journal of Organic Chemistry*, 1986, 51, pages 1882-1884). As another example, amine compounds (such as those of Formulas XIX-XXXI) can be reacted with a substituted carbodiimide compound to provide the compounds of the disclosure (e.g., N,N'-diisopropylcabodiimide [CAS Number 693-13-0], N,N'-dicyclohexylcarbodiimide [CAS Number 538-75-0], N-ethyl-N'(3-dimethylaminopropyl)carbodiimide [CAS Number 25952-53-8], 1,3-di-para-tolylcarbodiimide [CAS Number 726-42-1], 1,3-di-ortho-tolylcarbodiimide, etc.). As yet another example, amine compounds (such as those of Formulas XIX-XXXI) can be reacted with a substituted pyrazole-1-carboxamidine compound (such as for example N-propylpyrazole-1-carboxamidine hydrochloride, N-pentylpyrazole-1-carboxamidine hydrochloride, N-benzyl-1-carboxamidine hydrochloride, N-cyclopropylmethyl-1-carboxamidine hydrochloride, etc.) to provide the compounds of the disclosure [see Lee, *Bioorganic & Medicinal Chemistry Letters*, 2000, 10, pages 2771-2774; Lee, *Synthesis*, 1999, pages 1495-1499; and Examples 62-65 of International Patent Publication WO2005/051380 (Scobie)].

As a further example, amine compounds (such as those of Formulas XIX-XXXI) can be reacted with N,N'-bis-BOC-pyrazole-1-carboxamidine (CAS Number 152120-54-2) to form a di-Boc substituted guanidine (see Bernatowicz, *Tetrahedron Letters*, 1993, 34, pages 3389-3392).

General synthetic methods that are useful for the preparation of the intermediate amines of Formulas XIX-XXXI have been previously described and many of the intermediate amine compounds are known compounds. References for the preparation of the intermediate amine compounds are incorporated by reference and include U.S. Pat. No. 7,799,800 (Wightman, see Example 1 Parts A-J), U.S. Pat. No. 7,115,622 (Crooks, see Reaction Schemes II, III, V and Examples 1-3,5, 67-69), U.S. Pat. No. 7,579,359 (Krepski, see Reaction Schemes VI and VII), U.S. Patent Application 2013/0230578 (Wightman, see Example 1 Parts A-D), U.S. Pat. No. 7,163,947 (Griesgraber, see Scheme VII and Example 14 Parts A-F), U.S. Pat. No. 6,069,149 (Nanba, see Examples 5, 10, 12, 17, 20-21, 28, 33, 39), U.S. Pat. No. 8,728,486 (David, see Compound 7c and 7d), U.S. Pat. No. 7,968,563 (Kshirsagar), U.S. Pat. No. 8,088,790 (Kshirsagar, see Scheme IV, Example 8 Parts A-D, Example 56 Parts A-D, Example 62 Parts A-E), U.S. Pat. No. 8,168,802 (Hays), U.S. Pat. No. 9,034,336 (Ferguson), U.S. Pat. No. 7,884,207 (Stoermer, see Scheme VII, Example 286 Parts A-B, Example 339 Parts A-D).

Some examples of intermediate amine compounds that can be converted into the guanidine compounds of the disclosure are shown in Formulas XIX-XXXI, wherein $R_2$, $R_{2A}$, $R_{2B}$, $R_{2C}$, $R_3$, $R_{3C}$, $R_4$, $R_{4C}$, $R_7$, $R_{7B}$, $R_A$, $R_C$, V, W, X, $X_B$, Y, Z, $Z_B$, m, J, K, q can be as defined in any of the embodiments above.

In the preparation of the compounds of the disclosure it is understood by one of ordinary skill in the art that it may be necessary to protect a particular functional group while reacting other functional groups of an intermediate compound. The need for such protection will vary depending on the nature of the particular functional group and the conditions of the particular reaction step. A review of reactions for protecting and deprotecting functional groups can be found in T. W. Greene and P. G. M. Wuts, *Protective Groups in Organic Synthesis*, John Wiley & Sons, New York, USA, 1991.

Conventional methods and techniques of separation and purification can be used to isolate the IRM compounds used in the formulations of the disclosure. Such techniques may include, for example, all types of chromatography (high performance liquid chromatography (HPLC), column chromatography using common absorbents such as silica gel, and thin layer chromatography), recrystallization, and differential (i.e., liquid-liquid) extraction techniques.

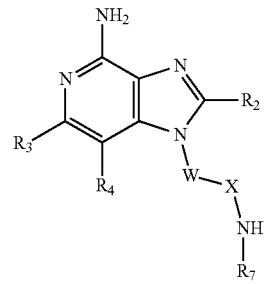

Formula XIX

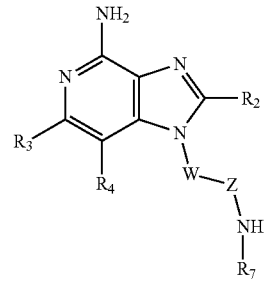

Formula XX

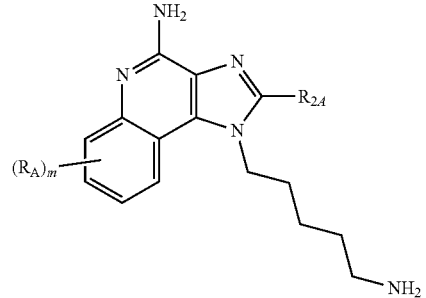

Formula XXI

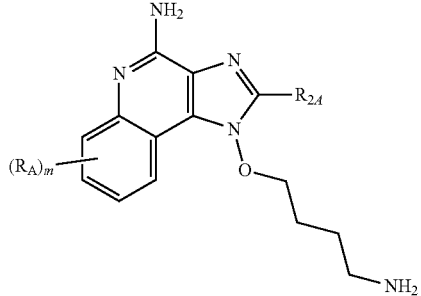

Formula XXII

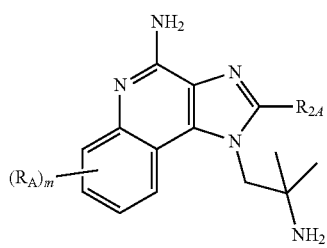

Formula XXIII

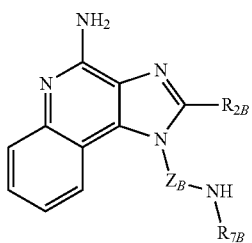

Formula XXIX

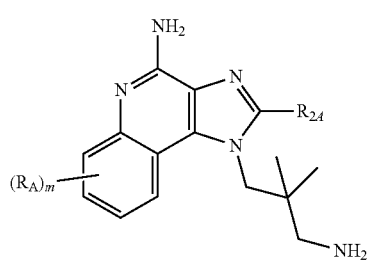

Formula XXIV

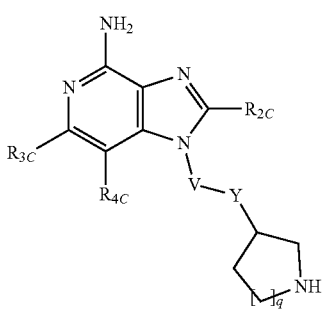

Formula XXX

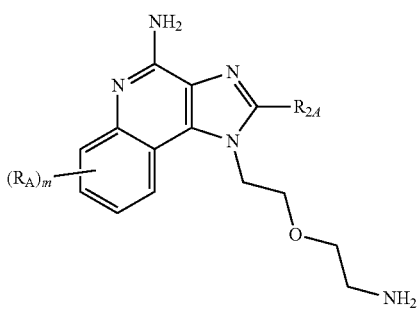

Formula XXV

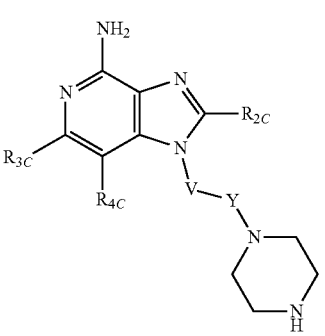

Formula XXXI

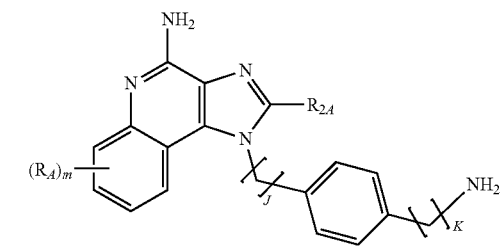

Formula XXVI

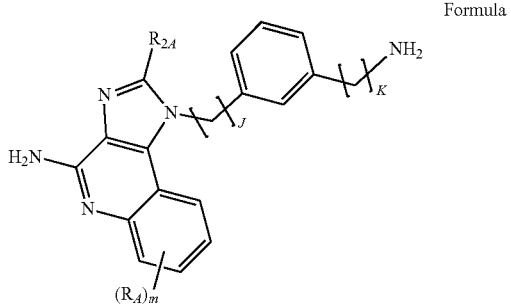

Formula XXVII

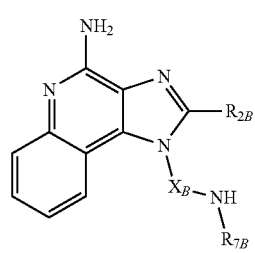

Formula XXVIII

It is understood that for Formulas I-V and XIII, when "Q" is a covalent bond the resulting ring that is formed is a cyclopropane ring; when "Q" is —CH$_2$— the resulting ring that is formed is a cyclobutane ring; when "Q" is —CH$_2$CH$_2$CH$_2$— the resulting ring that is formed is a cyclohexane ring; and when "Q" is —CH$_2$OCH$_2$— the resulting ring that is formed is a tetrahydropyran ring.

When a group (or substituent or variable) is present more than once in any Formula described herein, each group (or substituent or variable) is independently selected, whether explicitly stated or not. For example, for a Formula containing "—X-arylene-X—" each "X" group is independently selected.

For simplicity and convenience, it is understood that some of the compounds of the disclosure may be drawn in a certain isomeric form, but in fact all stereoisomers [i.e. configurational isomers (e.g. E,Z isomers), conformational isomers (e.g. rotational isomers), diastereomers, enantiomers] are expressly included within the scope of this disclosure (whether explicitly drawn or not).

Specifically, it is understood that for compounds of Formulas I-XVIII, all stereoisomers [i.e. configurational isomers (e.g. E,Z isomers), conformational isomers (e.g. rotational isomers), diastereomers, enantiomers] are expressly included (whether explicitly drawn or not).

Compounds or salts of the present disclosure may exist in different tautomeric forms, and it is understood that all such forms are expressly included within the scope of this disclosure. Specifically, it is understood that for compounds of Formulas I—, all tautomers are expressly included (whether explicitly drawn or not).

Prodrugs of the disclosed compounds can also be prepared by attaching to the compounds a functional group that can be cleaved under physiological conditions. Typically a cleavable functional group will be cleaved in vivo by various mechanisms (such a through a chemical (e.g., hydrolysis) or enzymatic transformation) to yield a compound of the disclosure. A discussion of the use of prodrugs is provided by T. Higuchi and W. Stella. "Prodrugs as Novel Delivery Systems", vol. 14 of the ACS Symposium Series, and in Bioreversible Carriers in Drug Design, ed. Edward B. Roche, American Pharmaceutical Association and Pergamon Press, 1987.

For any of the compounds of Formula I presented herein, each one of the variables R, $R_1$, $R_2$, $R_3$, $R_4$, $R_5$, $R_6$, $R_7$, Q, W, X, Z in any of the Formula I embodiments can be combined with any one or more of the other variables in any of the Formula I embodiments, as would be understood by one of ordinary skill in the art. Each of the resulting combinations of variables is also an embodiment of the disclosure.

For any of the compounds of Formula II-V presented herein, each one of the variables R, $R_1$, $R_2$, $R_5$, $R_6$, $R_7$, n, Q, W, X, Z in any of the Formula II-V embodiments can be combined with any one or more of the other variables in any of the Formula II-V embodiments, as would be understood by one of ordinary skill in the art. Each of the resulting combinations of variables is also an embodiment of the disclosure.

For any of the compounds of Formula VI-XII presented herein, each one of the variables $R_A$, $R_{2A}$, $R_{5A}$, $R_{6A}$, m, J, K in any of the Formula VI-XII embodiments can be combined with any one or more of the other variables in any of the Formula VI-XII embodiments, as would be understood by one of ordinary skill in the art. Each of the resulting combinations of variables is also an embodiment of the disclosure.

For any of the compounds of Formula XIII presented herein, each one of the variables $R_{1B}$, $R_{2B}$, $R_{5B}$, $R_{6B}$, $R_{7B}$, Q, $X_B$, $Z_B$ in any of the Formula XIII embodiments can be combined with any one or more of the other variables in any of the Formula XIII embodiments, as would be understood by one of ordinary skill in the art. Each of the resulting combinations of variables is also an embodiment of the disclosure.

For any of the compounds of Formula XIV presented herein, each one of the variables $R_C$, $R_{1C}$, $R_{2C}$, $R_{3C}$, $R_{4C}$, $R_{5C}$, $R_{6C}$, V, Y, q, t in any of the Formula XIV embodiments can be combined with any one or more of the other variables in any of the Formula XIV embodiments, as would be understood by one of ordinary skill in the art. Each of the resulting combinations of variables is also an embodiment of the disclosure.

For any of the compounds of Formula XV-XVIII presented herein, each one of the variables $R_C$, $R_{1C}$, $R_{2C}$, $R_{5C}$, $R_{6C}$, V, Y, p, q, t in any of the Formula XV-XVIII embodiments can be combined with any one or more of the other variables in any of the Formula XV-XVIII embodiments, as would be understood by one of ordinary skill in the art. Each of the resulting combinations of variables is also an embodiment of the disclosure.

Pharmaceutical Compositions and Biological Activity

Pharmaceutical compositions of the disclosure are also contemplated. Pharmaceutical compositions of the disclosure contain a therapeutically effective amount of a compound or salt of the disclosure (described herein) in combination with a pharmaceutically acceptable carrier.

The exact amount of compound or salt used in a pharmaceutical composition of the disclosure will vary according to factors known to those of skill in the art, such as the physical and chemical nature of the compound or salt, the nature of the carrier, and the intended dosing regimen.

The exact amount of compound or salt used in a pharmaceutical composition of the disclosure will vary according to factors known to those of skill in the art, such as the physical and chemical nature of the compound or salt, the nature of the carrier, and the intended dosing regimen.

In some embodiments, the compositions of the disclosure will contain sufficient active ingredient or prodrug to provide a dose of about 100 nanograms per kilogram (ng/kg) to about 50 milligrams per kilogram (mg/kg), preferably about 10 micrograms per kilogram (rig/kg) to about 5 mg/kg, of the compound or salt to the subject.

In some embodiments, the compositions of the disclosure will contain sufficient active ingredient or prodrug to provide a dose of for example, from about 0.01 mg/m$^2$ to about 5.0 mg/m$^2$, computed according to the Dubois method, in which the body surface area of a subject (m$^2$) is computed using the subject's body weight: m$^2$=(wt kg$^{0.425}$×height cm$^{0.725}$)×0.007184, although in some embodiments the methods may be performed by administering a compound or salt or composition in a dose outside this range. In some of these embodiments, the method includes administering sufficient compound to provide a dose of from about 0.1 mg/m$^2$ to about 2.0 mg/m$^2$ to the subject, for example, a dose of from about 0.4 mg/m$^2$ to about 1.2 mg/m$^2$.

A variety of dosage forms may be used to administer the compounds or salts of the disclosure to an animal. Dosage forms that can be used include, for example, tablets, lozenges, capsules, parenteral formulations, creams, ointments, topical gels, aerosol formulations, liquid formulations (e.g., aqueous formulation), transdermal patches, and the like. These dosage forms can be prepared with conventional pharmaceutically acceptable carriers and additives using conventional methods, which generally include the step of bringing the active ingredient into association with the carrier. A preferred dosage form has one or more of compounds or salts of the disclosure dissolved in an aqueous formulation.

Compounds or salts disclosed herein induce the production of certain cytokines in experiments performed according to the description of the Examples. These results indicate that the compounds or salts are useful for enhancing the immune response in a number of different ways, making them useful in the treatment of a variety of disorders.

The compounds or salts described herein can be administered as the single therapeutic agent in the treatment regimen, or the compounds or salts described herein may be administered in combination with one another or with other active agents, including additional immune response modifiers, antivirals, antibiotics, proteins, peptides, oligonucleotides, antibodies, etc.

Compounds or salts described herein induce the production of cytokines (e.g., IFN-alpha, IFN-gamma, TNF-alpha, IP-10) in experiments performed according to the tests set forth below. These results indicate that the compounds of the disclosure or salts are useful for activating the immune response in a number of different ways, rendering them useful in the treatment of a variety of disorders. As such, the compounds or salts of the disclosure (compounds or salts of Formulas I-XVIII) are agonists of cytokine biosynthesis and production, particularly agonists of IFN-alpha, IFN-gamma, TNF-alpha, and IP-10 cytokine biosynthesis and production.

It is believed that one way in which the compounds or salts of the disclosure (Formulas I-XVIII) induce cytokine production is through the activation of Toll-like receptors (TLRs) in the immune system, particularly TLR-7 and/or TLR-8, however other mechanisms may be involved. It is believed that in the immune system pathways (i.e. mechanisms) for cytokine induction, the compounds or salts of the disclosure (Formulas I-XVIII) primarily act as agonists of TLR-7 and/or TLR-8, however other pathways or activities may be involved.

Administration of the compounds or salts described herein can induce the production of interferon-alpha (IFN-alpha), interferon-gamma (IFN-gamma), tumor necrosis factor-alpha (TNF-alpha), and IP-10 in cells. Cytokines whose biosynthesis can be induced by compounds or salts of the disclosure include IFN-alpha, IFN-gamma, TNF-alpha, IP-10, and a variety of other cytokines. Among other effects, these cytokines can inhibit virus production and tumor cell growth, making the compounds or salts useful in the treatment of viral diseases and neoplastic diseases. Accordingly, the disclosure provides a method of inducing cytokine biosynthesis in an animal by administering an effective amount of a compound or salt of the disclosure to the animal. The animal to which the compound or salt is administered for induction of cytokine production may have one or more diseases, disorders, or conditions described below, for example a viral disease or a neoplastic disease, and administration of the compound or salt may provide therapeutic treatment. Alternatively, the compound or salt may be administered to the animal prior to the animal acquiring the disease so that administration of the compound or salt may provide a prophylactic treatment.

In addition to the ability to induce the production of cytokines, compounds or salts described herein can affect other aspects of the innate immune response. For example, natural killer cell activity may be stimulated, an effect that may be due to cytokine induction. The compounds or salts may also activate macrophages, which in turn stimulate secretion of nitric oxide and the production of additional cytokines. In addition, the compounds or salts may cause proliferation and differentiation of B-lymphocytes.

Conditions for which compounds or salts or compositions identified herein may be used as treatment include, but are not limited to:

Viral diseases such as, for example, diseases resulting from infection by an adenovirus, a herpes virus (e.g., HSV-I, HSV-II, CMV, or VZV), a poxvirus (e.g., an orthopoxvirus such as variola or vaccinia, or molluscum contagiosum), a picornavirus (e.g., rhinovirus or enterovirus), an orthomyxovirus (e.g., influenzavirus, avian influenza), a paramyxovirus (e.g., parainfluenzavirus, mumps virus, measles virus, and respiratory syncytial virus (RSV), a coronavirus (e.g., SARS), a papovavirus (e.g., papillomaviruses, such as those that cause genital warts, common warts, or plantar warts), hepadnavirus (e.g., hepatitis B virus), a flavivirus (e.g., hepatitis C virus or Dengue virus), or a retrovirus (e.g., a lentivirus such as HIV), ebolavirus;

Neoplastic diseases such as bladder cancer, cervical dysplasia, actinic keratosis, basal cell carcinoma, cutaneous T-cell lymphoma, mycosis fungoides, Sezary Syndrome, HPV associated head and neck cancer (e.g., HPV positive oropharyngeal squamous cell carcinoma), Kaposi's sarcoma, melanoma, squamous cell carcinoma, renal cell carcinoma, acute myeloid leukemia, chronic myeloid leukemia, chronic lymphocytic leukemia, multiple myeloma, Hodgkin's lymphoma, non-Hodgkin's lymphoma, B-cell lymphoma, hairy cell leukemia, esophageal cancer, and other cancers;

$T_H2$-mediated atopic diseases such a atopic dermatitis or eczema, eosinophilia, asthma, allergy, allergic rhinitis, and Ommen's syndrome;

Diseases associated with wound repair, such as, for example, inhibition of keloid formation and other types of scarring (e.g., enhancing wound healing, including chronic wounds);

Parasitic diseases including but not limited to malaria, leishmaniasis, cryptosporidiosis, toxoplasmosis, and trypanosome infection.

In addition, a compound, salt, or composition described herein may be used as a vaccine adjuvant for use in conjunction with any material that increases either humoral and/or cell mediated immune responses, such as, for example, tumor antigens (e.g., MAGE-3, NY-ESO-1); live viral, bacterial, or parasitic immunogens; inactivated viral, protozoal, fungal, or bacterial immunogens; toxoids; toxins; polysaccharides; proteins; glycoproteins; peptides; cellular vaccines; DNA vaccines; autologous vaccines; recombinant proteins; and the like.

Examples of vaccines that can benefit from use of a compound, salt, or composition identified herein as a vaccine adjuvant include BCG vaccine, cholera vaccine, plague vaccine, typhoid vaccine, haepatitis A vaccine, hepatitis B vaccine, hepatitis C vaccine, influenza A vaccine, influenza B vaccine, parainfluenza vaccine, polio vaccine, rabies vaccine, measles vaccine, mumps vaccine, rubella vaccine, yellow fever vaccine, tetanus vaccine, diphtheria vaccine, hemophilus influenza b vaccine, tuberculosis vaccine, meningococcal and pneumococcal vaccines, adenovirus vaccine, HIV vaccine, chicken pox vaccine, cytomegalovirus vaccine, dengue vaccine, feline leukemia vaccine, fowl plague vaccine, HSV-1 vaccine and HSV-2 vaccine, hog cholera vaccine, Japanese encephalitis vaccine, respiratory syncytial virus vaccine, rotavirus vaccine, papilloma virus vaccine, yellow fever vaccine, ebola virus vaccine.

Compounds, salts, or compositions identified herein may be particularly useful as vaccine adjuvants when used in conjunction with tumor antigens associated with colorectal cancer, head and neck cancer, breast cancer, lung cancer and melanoma.

Compounds, salts, or compositions identified herein may be particularly useful in individuals having compromised immune function. For example, compounds, salts, or compositions may be used for treating opportunistic infections and tumors that occur after suppression of cell mediated immunity in, for example, transplant patients, cancer patients, and HIV patients.

One or more of the above diseases or types of diseases, for example, a viral disease or neoplastic disease may be treated in an animal in need thereof (having the disease) by administering a therapeutically effective amount of a compound, salt, or composition to the animal.

An animal may also be vaccinated by administering an effective amount of a compound, salt, or composition described herein as a vaccine adjuvant. In one embodiment, a method of vaccinating an animal includes administering an effective amount of a compound, salt, or composition described herein to the animal as a vaccine adjuvant. The vaccine adjuvant can be co-administered with the material that increases one or more humoral and cell mediated immune responses by including each in the same composition. Alternatively, the vaccine adjuvant and the material that increases either humoral and/or cell mediated immune responses can be in separate compositions.

Compounds or salts or compositions identified herein may be particularly useful when an effective amount is administered to an animal to treat bladder cancer, cervical dysplasia, actinic keratosis, basal cell carcinoma, genital warts, herpes virus infection, or cutaneous T-cell lymphoma. For these conditions, administration of the compound, salt, or composition of the disclosure is preferably topical (i.e. applied directly to the surface of a tumor, a lesion, a wart, or an infected tissue, etc).

In one embodiment an effective amount of compound, salt, or composition described herein, such as an aqueous composition is administered into the bladder of an animal that has at least one tumor of the bladder by intravesical instillation (e.g., administration using a catheter).

An amount of a compound or salt effective to induce cytokine biosynthesis will typically cause one or more cell types, such as monocytes, macrophages, dendritic cells, and B-cells to produce an amount of one or more cytokines, such as, for example, IFN-alpha, IFN-gamma, TNF-alpha, and IP-10 that is increased (induced) over a background level of such cytokines. The precise dose will vary according to factors known in the art but is typically to be a dose of about 100 ng/kg to about 50 mg/kg, preferably about 10 µg/kg to about 5 mg/kg. In other embodiments, the amount can be, for example, from about 0.01 mg/m$^2$ to about 5.0 mg/m$^2$, (computed according to the Dubois method as described above) although in other embodiments the induction of cytokine biosynthesis may be performed by administering a compound or salt in a dose outside this range. In some of these embodiments, the method includes administering sufficient compound or salt or composition to provide a dose from about 0.1 mg/m$^2$ to about 2.0 mg/m$^2$ to the subject, for example, a dose of from about 0.4 mg/m$^2$ to about 1.2 mg/m$^2$.

A method of treating a viral infection in an animal and a method of treating a neoplastic disease in an animal can include administering an effective amount of at least one compound or salt described herein to the animal. An effective amount to treat or inhibit a viral infection can be an amount that will cause a reduction in one or more of the manifestations of viral infection, such as viral lesions, viral load, rate of virus production, and mortality as compared to untreated control animals. The precise amount that is effective for such treatment will vary according to factors known in the art but it is normally a dose of about 100 ng/kg to about 50 mg/kg, preferably about 10 µg/kg to about 5 mg/kg. An amount of a compound or salt effective to treat a neoplastic condition can be an amount that causes a reduction in tumor size or in the number of tumor foci. The precise amount will vary according to factors known in the art but is typically about 100 ng/kg to about 50 mg/kg, preferably about 10 µg/kg to about 5 mg/kg. In other embodiments, the amount is typically, for example, from about 0.01 mg/m$^2$ to about 5.0 mg/m$^2$, (computed according to the Dubois method as described above) although in some embodiments the induction of cytokine biosynthesis may be performed by administering a compound or salt in a dose outside this range. In some of these embodiments, the method includes administering sufficient compound or salt or composition to provide a dose from about 0.1 mg/m$^2$ to about 2.0 mg/m$^2$ to the subject, for example, a dose of from about 0.4 mg/m$^2$ to about 1.2 mg/m$^2$.

EMBODIMENTS

Embodiment 1 is a compound of Formula (I):

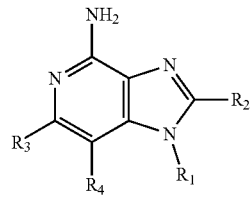

Formula I wherein:

$R_3$ and $R_4$ are taken together to form a fused benzene ring, a fused pyridine ring, a fused cyclohexene ring, or a fused tetrahydropyridine ring; wherein the fused benzene ring, fused pyridine ring, fused cyclohexene ring, or fused tetrahydropyridine ring is either unsubstituted or substituted by one or more R groups;

R is selected from the group consisting of halogen, hydroxyl, alkyl, alkoxy, haloalkyl, —C(O)—O-alkyl, —C(O)—OCH$_2$Ph, —C(O)—O-aryl, amino, alkylamino, and dialkylamino, aryl, arylalkylenyl, aryloxyalkylenyl, arylalkyleneoxy, aryloxy, heteroaryl, heteroarylalkylenyl, heteroaryloxyalkyenyl, heteroarylalkyleneoxy, and heteroaryloxy, wherein the alkyl, aryl, arylalkylenyl, aryloxyalkylenyl, arylalkyleneoxy, aryloxy, heteroaryl, heteroarylalkylenyl, heteroaryloxyalkyenyl, heteroarylalkyleneoxy, and heteroaryloxy groups can be unsubstituted or substituted by one or more substituents independently selected from the group consisting of alkyl, alkoxy, halogen, haloalkyl, hydroxyl, hydroxyalkylenyl, alkoxyalkylenyl, arylalkyleneoxy, and nitrile;

$R_1$ is selected from the group consisting of —W—X—N($R_7$)—C(=N—$R_5$)—N(H)$R_6$, —W—Z—N($R_7$)—C(=N—$R_5$)—N(H)$R_6$, and

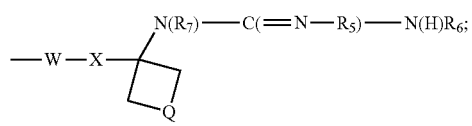

W is selected from the group consisting of a covalent bond, —O—, and —NH—;

X is selected from the group consisting of alkylene, alkenylene, and alkynylene, wherein any of the alkylene, alkenylene, and alkynylene groups can be optionally interrupted by one or more —O— groups;

Z is selected from the group consisting of
—X-arylene-X—,
—X-heteroarylene-X—,
—X-arylene-, and
—X-heteroarylene-;

$R_2$ is selected from the group consisting of hydrogen, alkyl, alkenyl, alkynyl, —O-alkyl, hydroxyalkylenyl, alkoxyalkylenyl, alkylaminoalkylenyl, hydroxyl, —CH$_2$—NH—O-alkyl, and —CH$_2$NHC(O)-alkyl;

$R_7$ is selected from the group consisting of hydrogen, alkyl, arylalkylenyl, alkoxyalkylenyl, aryloxyalkylenyl, benzyloxyalkylenyl, aryl-(CH$_2$)$_{2-6}$—O-alkylenyl, and cycloalkylalkylenyl, wherein any of the alkyl, arylalkylenyl, alkoxyalkylenyl, aryloxyalkylenyl, benzyloxyalkylenyl, aryl- $(CH_2)_{2-6}$—O-alkylenyl, and cycloalkylalkylenyl groups can be either unsubstituted or substituted with one or more substituents independently selected from the group consisting of halogen, hydroxyl, alkoxy, alkyl, haloalkyl, and nitrile;

Q is selected from the group consisting of a bond, —$CH_2$—, —$CH_2CH_2$—, —$CH_2CH_2CH_2$—, —$CH_2CH_2CH_2CH_2$—, —$CH_2CH_2CH_2CH_2CH_2$—, —$CH_2$—O—$CH_2$—, and —$OCH_2$—;

$R_5$ and $R_6$ are independently selected from the group consisting of hydrogen, —C(O)—O-alkyl, alkyl, cycloalkyl, aryl, arylalkylenyl, aryloxyalkylenyl, heteroaryl, heteroarylalkylenyl, heteroaryloxyalkylenyl, cycloalkylalkylenyl, aryl-$(CH_2)_{2-6}$—O-alkylenyl, and benzyloxyalkylenyl; wherein any of the alkyl, cycloalkyl, aryl, arylalkylenyl, aryloxyalkylenyl, heteroaryl, heteroarylalkylenyl, heteroaryloxyalkylenyl, cycloalkylalkylenyl, aryl-$(CH_2)_{2-6}$—O-alkylenyl, and benzyloxyalkylenyl groups can be either unsubstituted or substituted with one or more substituents independently selected from the group consisting of halogen, hydroxyl, alkoxy, alkyl, haloalkyl, cycloalkyl, nitrile, aryl, heteroaryl, and dialkylamino; with the proviso that $R_5$ and $R_6$ are not both hydrogen;

or a pharmaceutically acceptable salt thereof.

Embodiment 2 is the compound or salt of embodiment 1, wherein $R_3$ and $R_4$ are taken together to form a fused benzene ring, a fused pyridine ring, or a fused cyclohexene ring.

Embodiment 3 is the compound or salt of any one of the embodiments 1-2, wherein $R_3$ and $R_4$ are taken together to form a fused benzene ring, a fused pyridine ring, or a fused cyclohexene ring, and wherein the fused benzene ring, fused pyridine ring, or fused cyclohexene ring is either unsubstituted or substituted by one and only one R group.

Embodiment 4 is the compound or salt of any one of the embodiments 1-3, wherein $R_3$ and $R_4$ are taken together to form a fused benzene ring or a fused cyclohexene ring, and wherein the fused benzene ring, or fused cyclohexene ring is either unsubstituted or substituted by one and only one R group.

Embodiment 5 is the compound or salt of any one of the embodiments 1-3, wherein $R_3$ and $R_4$ are taken together to form a fused benzene ring or a fused pyridine ring, and wherein the fused benzene ring, or fused pyridine ring is either unsubstituted or substituted by one and only one R group.

Embodiment 6 is the compound or salt of any one of the embodiments 1-5, wherein R is selected from the group consisting of hydroxyl, F, Cl, —$CF_3$, —$OCF_3$, —O—$C_{1-6}$alkyl, and —$C_{1-6}$alkyl.

Embodiment 7 is the compound or salt of any one of the embodiments 1-5, wherein R is selected from the group consisting of hydroxyl, F, Cl, —$CF_3$, —$OCH_3$, —$OCF_3$, —$OCH_2CH_3$, —$OCH(CH_3)_2$, —$CH_3$, —$CH_2CH_3$, —$CH_2CH_2CH_3$, and —$CH(CH_3)_2$.

Embodiment 8 is the compound or salt of any one of the embodiments 1-5, wherein R is —C(O)O$C_{1-4}$ alkyl.

Embodiment 9 is the compound or salt of any one of the embodiments 1-5, wherein R is selected from the group consisting of —$CO_2CH_3$, —$CO_2CH_2CH_3$, —$CO_2CH(CH_3)_2$, —$CO_2CH_2CH_2CH_3$, —$CO_2CH_2CH_2CH_2CH_3$, —$CO_2$—$CH_2Ph$, and —$CO_2CH_2CH(CH_3)_2$.

Embodiment 10 is the compound or salt of any one of the embodiments 1-9, wherein $R_7$ is hydrogen, alkyl, or —$CH_2Ph$.

Embodiment 11 is the compound or salt of any one of the embodiments 1-10, wherein $R_7$ is hydrogen, $C_{1-8}$ alkyl, or —$CH_2Ph$.

Embodiment 12 is the compound or salt of any one of the embodiments 1-11, wherein $R_7$ is hydrogen or $C_{1-4}$ alkyl.

Embodiment 13 is the compound or salt of any one of the embodiments 1-9, wherein $R_7$ is selected from the group consisting of hydrogen, —$CH_3$, —$CH_2CH_3$, —$CH(CH_3)_2$, —$CH_2CH_2CH_3$, —$CH_2CH_2CH_2CH_3$, —$CH_2CH(CH_3)_2$, —$C(CH_3)_3$, —$CH_2CH_2CH_2CH_2CH_3$, —$CH_2CH_2CH(CH_3)_2$, cyclopentyl, cyclohexyl, —$CH_2$(cyclopentyl), —$CH_2$(cyclohexyl), and —$CH_2CH_2$—O—$CH_3$.

Embodiment 14 is the compound or salt of any one of the embodiments 1-9, wherein $R_7$ is selected from the group consisting of hydrogen, alkyl, —$CH_2Ph$, —$CH_2CH_2Ph$, —$CH_2CH_2$—O-Ph, —$CH_2CH_2$—O—$CH_2Ph$, and —$(CH_2)_{2-6}$—O—$(CH_2)_{1-6}Ph$, wherein Ph can be either unsubstituted or substituted with one or more substituents independently selected from the group consisting of halogen, hydroxyl, alkyl, alkoxy, haloalkyl, and nitrile.

Embodiment 15 is the compound or salt of any one of the embodiments 1-14, wherein $R_1$ is selected from the group consisting of —W—X—N(H)—C(=N—$R_5$)—N(H)$R_6$, and —W—Z—N(H)—C(=N—$R_5$)—N(H)$R_6$.

Embodiment 16 is the compound or salt of any one of the embodiments 1-15, wherein W is a covalent bond or —O—.

Embodiment 17 is the compound or salt of any one of the embodiments 1-16, wherein X is alkylene optionally interrupted by one or more —O— groups.

Embodiment 18 is the compound or salt of any one of the embodiments 1-17, wherein X is selected from the group consisting of —$CH_2CH_2$—, —$CH_2CH_2CH_2$—, —$CH_2CH_2CH_2CH_2$—, —$CH_2CH_2CH_2CH_2CH_2$—, —$CH_2CH_2CH_2CH_2CH_2CH_2$—, —$CH_2CH_2CH_2CH_2CH_2CH_2CH_2$—, —$CH_2CH_2CH_2CH_2CH_2CH_2CH_2CH_2$—, —$CH_2C(CH_3)_2$—, —$CH_2C(CH_3)_2CH_2$—, —$CH_2CH_2$—O—$CH_2CH_2$—, —$CH_2CH_2$—O—$CH_2CH_2$—O—$CH_2CH_2$—, —$(CH_2)_{2-4}$—$(OCH_2CH_2$—$)_{1-5}$, and —$(CH_2)_{2-6}$—$(OCH_2CH_2$—$)_{1-4}$.

Embodiment 19 is the compound or salt of any one of the embodiments 1-18, wherein Z is —$C_{1-5}$alkylene-arylene-$C_{1-5}$alkylene- or —$C_{1-5}$alkylene-heteroarylene-$C_{1-5}$alkylene-.

Embodiment 20 is the compound or salt of any of the embodiments 1-19, wherein Z is —$CH_2$-phenylene-$CH_2$—.

Embodiment 21 is the compound or salt of any one of the embodiments 1-20, $R_2$ is selected from the group consisting hydrogen, alkyl, alkoxyalkylenyl, alkylaminoalkylenyl, and hydroxyalkylenyl.

Embodiment 22 is the compound or salt of any one of the embodiments 1-21, wherein $R_2$ is selected from the group consisting of hydrogen, —$CH_3$, —$CH_2CH_3$, —$CH_2CH_2CH_3$, —$CH_2CH_2CH_2CH_3$, —$CH_2OCH_3$, —$CH_2OCH_2CH_3$, —$CH_2CH_2OCH_3$, —$CH_2NHCH_3$, —$CH_2NHCH_2CH_3$, —$CH_2CH_2NHCH_3$, —$CH_2OH$, and —$CH_2CH_2OH$.

Embodiment 23 is the compound or salt of any one of the embodiments 1-22, wherein $R_2$ is selected from the group consisting of hydrogen, —$CH_3$, —$CH_2CH_3$, —$CH_2CH_2CH_3$, —$CH_2CH_2CH_2CH_3$, —$CH_2OCH_3$, —$CH_2OCH_2CH_3$, and —$CH_2CH_2OCH_3$.

Embodiment 24 is the compound or salt of any one of the embodiments 1-20, wherein $R_2$ is —$CH_2NHOCH_3$, —$CH_2NHC(O)CH_3$ or —$CH_2NHC(O)$cyclopropyl.

Embodiment 25 is the compound or salt of any one of the embodiments 1-24, wherein $R_5$ and $R_6$ are independently selected from the group consisting of hydrogen, alkyl, phenyl, and phenylalkylenyl, and wherein $R_5$ and $R_6$ are not both hydrogen.

Embodiment 26 is the compound or salt of any one of the embodiments 1-25, wherein $R_5$ and $R_6$ are independently selected from the group consisting of alkyl, phenyl, and phenylalkylenyl.

Embodiment 27 is the compound or salt of any one of the embodiments 1-26, wherein $R_5$ is alkyl and $R_6$ is alkyl.

Embodiment 28 is the compound or salt of any one of the embodiments 1-27, wherein $R_5$ is $C_{1-8}$alkyl and $R_6$ is $C_{1-8}$alkyl.

Embodiment 29 is the compound or salt of any one of the embodiments 1-28, wherein $R_5$ is $C_{1-4}$alkyl and $R_6$ is $C_{1-4}$alkyl.

Embodiment 30 is the compound or salt of any one of the embodiments 1-24, wherein $R_5$ and $R_6$ are independently selected from the group consisting of alkyl, cycloalkyl, aryl, arylalkylenyl, aryloxyalkylenyl, heteroaryl, heteroarylalkylenyl, heteroaryloxyalkylenyl, cycloalkylalkylenyl, aryl-$(CH_2)_{2-6}$—O-alkylenyl, and benzyloxyalkylenyl; wherein any of the alkyl, cycloalkyl, aryl, arylalkylenyl, aryloxyalkylenyl, heteroaryl, heteroarylalkylenyl, heteroaryloxyalkylenyl, cycloalkylalkylenyl, aryl-$(CH_2)_{2-6}$—O-alkylenyl, and benzyloxyalkylenyl groups can be either unsubstituted or substituted with one or more substituents independently selected from the group consisting of halogen, hydroxyl, alkoxy, alkyl, haloalkyl, cycloalkyl, nitrile, aryl, heteroaryl, and dialkylamino.

Embodiment 31 is the compound or salt of any one of the embodiments 1-24, wherein $R_5$ and $R_6$ are independently selected from the group consisting of hydrogen, —$CH_3$, —$CH_2CH_3$, —$CH(CH_3)_2$, —$CH_2CH_2CH_3$, —$CH_2CH_2CH_2CH_3$, —$CH_2CH(CH_3)_2$, —$C(CH_3)_3$, —$CH_2CH_2CH_2CH_2CH_3$, —$(CH_2)_{5-9}CH_3$, —$CH_2CH_2CH(CH_3)_2$, cyclopropyl, cyclopentyl, cyclohexyl, —$CH_2$-cyclopropyl, —$CH_2$-cyclopentyl, —$CH_2$-cyclohexyl, —$CH_2CH_2$—O—$CH_3$, —$(CH_2)_{3-8}$—O—$CH_3$, and —$CH_2CH_2CH_2N(CH_3)_2$; wherein $R_5$ and $R_6$ are not both hydrogen.

Embodiment 32 is the compound or salt of any one of the embodiments 1-24, wherein $R_5$ and $R_6$ are independently selected from the group consisting of hydrogen, alkyl, —$CH_2Ph$, —$CH_2CH_2Ph$, —$CH_2CH_2$—O-Ph, -Ph, —$(CH_2)_{3-8}Ph$, —$(CH_2)_{3-8}$—O-Ph, —$CH_2CH_2$—O—$CH_2Ph$, —$(CH_2)_{3-8}$—O—$CH_2Ph$, and —$(CH_2)_{2-8}$—O—$(CH_2)_{1-4}Ph$, wherein the Ph group can be either unsubstituted or substituted with one or more substituents independently selected from the group consisting of halogen, hydroxyl, alkoxy, alkyl, haloalkyl, cycloalkyl, and nitrile; wherein $R_5$ and $R_6$ are not both hydrogen.

Embodiment 33 is the compound or salt of any one of the embodiments 1-32, wherein the pharmaceutically acceptable salt is hydrochloride.

Embodiment 34 is the compound or salt of any one of the embodiments 1-33, wherein the pharmaceutically acceptable salt is dihydrochloride.

Embodiment 35 is a compound of Formula XIII:

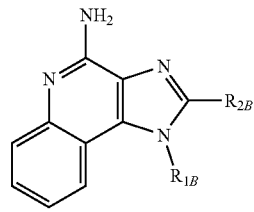

Formula XIII wherein:
$R_{1B}$ is selected from the group consisting of —$X_B$—N($R_{7B}$)—C(=N—$R_{5B}$)—N(H)$R_{6B}$, —$Z_B$—N($R_{7B}$)—C(=N—$R_{5B}$)—N(H)$R_{6B}$, and

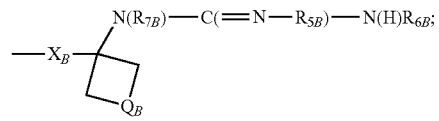

$X_B$ is selected from the group consisting of alkylene, alkenylene, and alkynylene, wherein the alkylene, alkenylene, and alkynylene groups can be optionally interrupted by one or more —O— groups;
$Z_B$ is selected from the group consisting of
—$X_B$-arylene-$X_B$—,
—$X_B$-heteroarylene-$X_B$—,
—$X_B$-arylene-, and
—$X_B$-heteroarylene-;
$R_{2B}$ is selected from the group consisting of hydrogen, alkyl, alkenyl, alkynyl, —O-alkyl, hydroxyalkylenyl, alkoxyalkylenyl, alkylaminoalkylenyl, hydroxyl, —$CH_2$—NH—O-alkyl, and —$CH_2NHC(O)$-alkyl;
$R_{7B}$ is selected from the group consisting of hydrogen, alkyl, arylalkylenyl, alkoxyalkylenyl, aryloxyalkylenyl, benzyloxyalkylenyl, aryl-$(CH_2)_{2-6}$—O-alkylenyl, and cycloalkylalkylenyl, wherein any of the alkyl, arylalkylenyl, alkoxyalkylenyl, aryloxyalkylenyl, benzyloxyalkylenyl, aryl-$(CH_2)_{2-6}$—O-alkylenyl, and cycloalkylalkylenyl groups can be either unsubstituted or substituted with one or more substituents independently selected from the group consisting of halogen, hydroxyl, alkoxy, alkyl, haloalkyl, and nitrile;
$Q_B$ is selected from the group consisting of a bond, —$CH_2$—, —$CH_2CH_2$—, —$CH_2CH_2CH_2$—, —$CH_2CH_2CH_2CH_2$—, —$CH_2CH_2CH_2CH_2CH_2$—, —$CH_2$—O—$CH_2$—, and —$OCH_2$—;
$R_{5B}$ and $R_{6B}$ are independently selected from the group consisting of hydrogen, —C(O)—O-alkyl, alkyl, cycloalkyl, aryl, arylalkylenyl, aryloxyalkylenyl, heteroaryl, heteroarylalkylenyl, heteroaryloxyalkylenyl, cycloalkylalkylenyl, aryl-$(CH_2)_{2-6}$—O-alkylenyl, and benzyloxyalkylenyl; wherein any of the alkyl, cycloalkyl, aryl, arylalkylenyl, aryloxyalkylenyl, heteroaryl, heteroarylalkylenyl, heteroaryloxyalkylenyl, cycloalkylalkylenyl, aryl-$(CH_2)_{2-6}$—O-alkylenyl, and benzyloxyalkylenyl groups can be either unsubstituted or substituted with one or more substituents independently selected from the group consisting of halogen, hydroxyl, alkoxy, alkyl, haloalkyl, cycloalkyl, nitrile, aryl, heteroaryl, and dialkylamino; with the proviso that $R_{5B}$ and $R_{6B}$ are not both hydrogen;
or a pharmaceutically acceptable salt thereof.

Embodiment 36 is the compound or salt of embodiment 35, wherein $R_{7B}$ is hydrogen, alkyl, or —$CH_2Ph$.

Embodiment 37 is the compound or salt of any one of the embodiments 35-36, wherein $R_{7B}$ is hydrogen, $C_{1-8}$ alkyl, or —$CH_2Ph$.

Embodiment 38 is the compound or salt of any one of the embodiments 35-37, wherein $R_{7B}$ is hydrogen or $C_{1-4}$ alkyl.

Embodiment 39 is the compound or salt of embodiment 35, wherein $R_{7B}$ is selected from the group consisting of hydrogen, —$CH_3$, —$CH_2CH_3$, —$CH(CH_3)_2$, —$CH_2CH_2CH_3$, —$CH_2CH_2CH_2CH_3$, —$CH_2CH(CH_3)_2$, —$C(CH_3)_3$, —$CH_2CH_2CH_2CH_2CH_3$, —$CH_2CH_2CH(CH_3)_2$, cyclopentyl, cyclohexyl, —$CH_2$(cyclopentyl), —$CH_2$(cyclohexyl), and —$CH_2CH_2$—O—$CH_3$.

Embodiment 40 is the compound or salt of embodiment 35, wherein $R_{7B}$ is selected from the group consisting of hydrogen, alkyl, —$CH_2Ph$, —$CH_2CH_2Ph$, —$CH_2CH_2$—O—Ph, —$CH_2CH_2$—O—$CH_2Ph$, and —$(CH_2)_{2-6}$—O—$(CH_2)_{1-6}Ph$, wherein Ph can be either unsubstituted or substituted with one or more substituents independently selected from the group consisting of halogen, hydroxyl, alkyl, alkoxy, and, nitrile.

Embodiment 41 is the compound or salt of embodiment 35-40, wherein $R_{1B}$ is selected from the group consisting of —$X_B$—N(H)—C(=N—$R_{5B}$)—N(H)$R_{6B}$, and —$Z_B$—N(H)—C(=N—$R_{5B}$)—N(H)$R_{6B}$.

Embodiment 42 is the compound or salt of any one of the embodiments 35-41, wherein $X_B$ is alkylene optionally interrupted by one or more —O— groups.

Embodiment 43 is the compound or salt of any one of the embodiments 35-42, wherein $X_B$ is selected from the group consisting of —$CH_2CH_2$—, —$CH_2CH_2CH_2$—, —$CH_2CH_2CH_2CH_2$—, —$CH_2CH_2CH_2CH_2CH_2$—, —$CH_2CH_2CH_2CH_2CH_2CH_2$—, —$CH_2CH_2CH_2CH_2CH_2CH_2CH_2$—, —$CH_2CH_2CH_2CH_2CH_2CH_2CH_2CH_2$—, —$CH_2C(CH_3)_2$—, —$CH_2C(CH_3)_2CH_2$—, —$CH_2CH_2$—O—$CH_2CH_2$—, —$CH_2CH_2$—O—$CH_2CH_2$—O—$CH_2CH_2$—, —$(CH_2)_{2-4}$—$(OCH_2CH_2$—$)_{1-5}$, and —$(CH_2)_{2-6}$—$(OCH_2CH_2$—$)_{1-4}$.

Embodiment 44 is the compound or salt of any one of the embodiments 35-43, wherein $Z_B$ is —$C_{1-5}$alkylene-arylene-$C_{1-5}$alkylene- or —$C_{1-5}$alkylene-heteroarylene-$C_{1-5}$alkylene-.

Embodiment 45 is the compound or salt of any of the embodiments 25-44, wherein $Z_B$ is —$CH_2$-phenylene-$CH_2$—.

Embodiment 46 is the compound or salt of any one of the embodiments 35-45, wherein $R_{2B}$ is selected from the group consisting hydrogen, alkyl, alkoxyalkylenyl, alkylaminoalkylenyl, and hydroxyalkylenyl.

Embodiment 47 is the compound or salt of any one of the embodiments 35-46, wherein $R_{2B}$ is selected from the group consisting of hydrogen, —$CH_3$, —$CH_2CH_3$, —$CH_2CH_2CH_3$, —$CH_2CH_2CH_2CH_3$, —$CH_2OCH_3$, —$CH_2OCH_2CH_3$, —$CH_2CH_2OCH_3$, —$CH_2NHCH_3$, —$CH_2NHCH_2CH_3$, —$CH_2CH_2NHCH_3$, —$CH_2OH$, and —$CH_2CH_2OH$.

Embodiment 48 is the compound or salt of any one of the embodiments 35-47, wherein $R_{2B}$ is selected from the group consisting of hydrogen, —$CH_3$, —$CH_2CH_3$, —$CH_2CH_2CH_3$, —$CH_2CH_2CH_2CH_3$, —$CH_2OCH_3$, —$CH_2OCH_2CH_3$, and —$CH_2CH_2OCH_3$.

Embodiment 49 is the compound or salt any one of the embodiments 35-45, wherein $R_2$ is —$CH_2NHOCH_3$, —$CH_2NHC(O)CH_3$ or —$CH_2NHC(O)$cyclopropyl.

Embodiment 50 is the compound or salt of any one of the embodiments 35-49, wherein $R_{5B}$ and $R_{6B}$ are independently selected from the group consisting of hydrogen, alkyl, phenyl, and phenylalkylenyl, and wherein $R_{5B}$ and $R_{6B}$ are not both hydrogen.

Embodiment 51 is the compound or salt of any one of the embodiments 35-50, wherein $R_{5B}$ and $R_{6B}$ are independently selected from the group consisting of alkyl, phenyl, and phenylalkylenyl.

Embodiment 52 is the compound or salt of any one of the embodiments 35-51, wherein $R_{5B}$ is alkyl and $R_{6B}$ is alkyl.

Embodiment 53 is the compound or salt of any one of the embodiments 35-52, wherein $R_{5B}$ is $C_{1-8}$alkyl and $R_{6B}$ is $C_{1-8}$alkyl.

Embodiment 54 is the compound or salt of any one of the embodiments 1-53, wherein $R_{5B}$ is $C_{1-4}$alkyl and $R_{6B}$ is $C_{1-4}$alkyl.

Embodiment 55 is the compound or salt of any one of the embodiments 35-49, wherein $R_{5B}$ and $R_{6B}$ are independently selected from the group consisting of alkyl, cycloalkyl, aryl, arylalkylenyl, aryloxyalkylenyl, heteroaryl, heteroarylalkylenyl, heteroaryloxyalkylenyl, cycloalkylalkylenyl, aryl-$(CH_2)_{2-6}$—O-alkylenyl, and benzyloxyalkylenyl; wherein any of the alkyl, cycloalkyl, aryl, arylalkylenyl, aryloxyalkylenyl, heteroaryl, heteroarylalkylenyl, heteroaryloxyalkylenyl, cycloalkylalkylenyl, aryl-$(CH_2)_{2-6}$—O-alkylenyl, and benzyloxyalkylenyl groups can be either unsubstituted or substituted with one or more substituents independently selected from the group consisting of halogen, hydroxyl, alkoxy, alkyl, haloalkyl, cycloalkyl, nitrile, aryl, heteroaryl, and dialkylamino.

Embodiment 56 is the compound or salt of any one of the embodiments 35-49, wherein, $R_{5B}$ and $R_{6B}$ are independently selected from the group consisting of hydrogen, —$CH_3$, —$CH_2CH_3$, —$CH(CH_3)_2$, —$CH_2CH_2CH_3$, —$CH_2CH_2CH_2CH_3$, —$CH_2CH(CH_3)_2$, —$C(CH_3)_3$, —$CH_2CH_2CH_2CH_2CH_3$, —$(CH_2)_{5-9}CH_3$, —$CH_2CH_2CH(CH_3)_2$, cyclopropyl, cyclopentyl, cyclohexyl, —$CH_2$-cyclopropyl, —$CH_2$-cyclopentyl, —$CH_2$-cyclohexyl, —$CH_2CH_2$—O—$CH_3$, —$(CH_2)_{3-8}$—O—$CH_3$, and —$CH_2CH_2CH_2N(CH_3)_2$; wherein $R_{5B}$ and $R_{6B}$ are not both hydrogen.

Embodiment 57 is the compound or salt of any one of the embodiments 35-49, wherein $R_{5B}$ and $R_{6B}$ are independently selected from the group consisting of hydrogen, alkyl, —$CH_2Ph$, —$CH_2CH_2Ph$, —$CH_2CH_2$—O-Ph, -Ph, —$(CH_2)_{3-8}Ph$, —$(CH_2)_{3-8}$—O-Ph, —$CH_2CH_2$—O—$CH_2Ph$, —$(CH_2)_{3-8}$—O—$CH_2Ph$, and —$(CH_2)_{2-8}$—O—$(CH_2)_{1-4}Ph$, wherein the Ph group can be either unsubstituted or substituted with one or more substituents independently selected from the group consisting of halogen, hydroxyl, alkoxy, alkyl, haloalkyl, cycloalkyl, and nitrile; and wherein $R_{5B}$ and $R_{6B}$ are not both hydrogen.

Embodiment 58 is the compound or salt of any one of the embodiments 35-57, wherein the pharmaceutically acceptable salt is hydrochloride.

Embodiment 59 is the compound or salt of any one of the embodiments 35-58, wherein the pharmaceutically acceptable salt is dihydrochloride.

Embodiment 60 is a method of inducing biosynthesis of IFN-alpha in an animal comprising administering an effective amount of a compound or salt of any one of the embodiments 1-59 to the animal.

Embodiment 61 is a method of inducing biosynthesis of IFN-gamma in an animal comprising administering an effective amount of a compound or salt of any one of the embodiments 1-59 to the animal.

Embodiment 62 is a method of inducing biosynthesis of TNF-alpha in an animal comprising administering an effective amount of a compound or salt of any one of the embodiments 1-59 to the animal.

Embodiment 63 is a method of inducing biosynthesis of IP-10 in an animal comprising administering an effective amount of a compound or salt of any one of the embodiments 1-59 to the animal.

Embodiment 64 is a method of inducing cytokine biosynthesis in an animal comprising administering an effective amount of a compound or salt of any one of the embodiments 1-59 to the animal.

Embodiment 65 is a pharmaceutical composition comprising a therapeutically effective amount of a compound or salt of embodiment 1 in combination with a pharmaceutically acceptable carrier.

Embodiment 66 is a pharmaceutical composition comprising a therapeutically effective amount of a compound or salt of any one of the embodiments 1-59 in combination with a pharmaceutically acceptable carrier.

Embodiment 67 is a compound of Formula XIV:

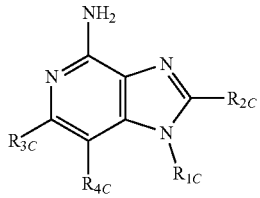

Formula XIV wherein:

$R_{3C}$ and $R_{4C}$ are taken together to form a fused benzene ring, a fused pyridine ring, a fused cyclohexene ring, or a fused tetrahydropyridine ring; wherein the fused benzene ring, fused pyridine ring, fused cyclohexene ring, or fused tetrahydropyridine ring is either unsubstituted or substituted by one or more $R_C$ groups;

$R_C$ is selected from the group consisting of halogen, hydroxyl, alkyl, alkoxy, haloalkylenyl, —C(O)—O-alkyl, —C(O)—OCH$_2$Ph, —C(O)—O-aryl, amino, alkylamino, and dialkylamino, aryl, arylalkylenyl, aryloxyalkylenyl, arylalkyleneoxy, aryloxy, heteroaryl, heteroarylalkylenyl, heteroaryloxyalkyenyl, heteroarylalkyleneoxy, and heteroaryloxy, wherein the alkyl, aryl, arylalkylenyl, aryloxyalkylenyl, arylalkyleneoxy, aryloxy, heteroaryl, heteroarylalkylenyl, heteroaryloxyalkyenyl, heteroarylalkyleneoxy, and heteroaryloxy groups can be unsubstituted or substituted by one or more substituents independently selected from the group consisting of alkyl, alkoxy, halogen, haloalkyl, hydroxyl, hydroxyalkylenyl, alkoxyalkylenyl, arylalkyleneoxy, and nitrile;

$R_{1C}$ is selected from the group consisting of

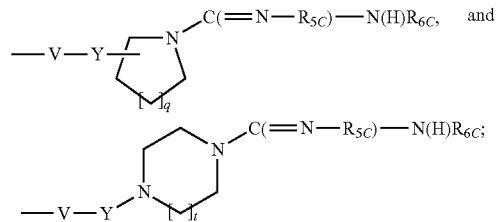

V is selected from the group consisting of a covalent bond, —O—, and —NH—;

Y is selected from the group consisting of alkylene, alkenylene, and alkynylene, wherein any of the alkylene, alkenylene, and alkynylene groups can be optionally interrupted by one or more —O— groups;

$R_{2C}$ is selected from the group consisting of hydrogen, alkyl, alkenyl, alkynyl, —O-alkyl, hydroxyalkylenyl, alkoxyalkylenyl, alkylaminoalkylenyl, hydroxyl, —CH$_2$—NH—O-alkyl, and —CH$_2$NHC(O)-alkyl;

$R_{5C}$ and $R_{6C}$ are independently selected from the group consisting of hydrogen, —C(O)—O-alkyl, alkyl, cycloalkyl, aryl, arylalkylenyl, aryloxyalkylenyl, heteroaryl, heteroarylalkylenyl, heteroaryloxyalkylenyl, cycloalkylalkylenyl, aryl-(CH$_2$)$_{2-6}$—O-alkylenyl, and benzyloxyalkylenyl; wherein any of the alkyl, cycloalkyl, aryl, arylalkylenyl, aryloxyalkylenyl, heteroaryl, heteroarylalkylenyl, heteroaryloxyalkylenyl, cycloalkylalkylenyl, aryl-(CH$_2$)$_{2-6}$—O-alkylenyl, and benzyloxyalkylenyl groups can be either unsubstituted or substituted with one or more substituents independently selected from the group consisting of halogen, hydroxyl, alkoxy, alkyl, haloalkyl, cycloalkyl, nitrile, aryl, heteroaryl, and dialkylamino; with the proviso that $R_{5C}$ and $R_{6C}$ are not both hydrogen.

q is an integer from 0 to 5;

t is an integer from 1 to 4;

or a pharmaceutically acceptable salt thereof.

Embodiment 68 is the compound or salt of embodiment 67, wherein $R_{3C}$ and $R_{4C}$ are taken together to form a fused benzene ring, a fused pyridine ring, or a fused cyclohexene ring.

Embodiment 69 is the compound or salt of any one of the embodiments 67-68, wherein $R_{3C}$ and $R_{4C}$ are taken together to form a fused benzene ring, a fused pyridine ring, or a fused cyclohexene ring, and wherein the fused benzene ring, fused pyridine ring, or fused cyclohexene ring is either unsubstituted or substituted by one and only one $R_C$ group.

Embodiment 70 is the compound or salt of any one of the embodiments 67-69, wherein $R_{3C}$ and $R_{4C}$ are taken together to form a fused benzene ring or a fused cyclohexene ring, and wherein the fused benzene ring, or fused cyclohexene ring is either unsubstituted or substituted by one and only one $R_C$ group.

Embodiment 71 is the compound or salt of any one of the embodiments 67-69, wherein $R_{3C}$ and $R_{4C}$ are taken together to form a fused benzene ring or a fused pyridine ring, and wherein the fused benzene ring, or fused pyridine ring is either unsubstituted or substituted by one and only one $R_C$ group.

Embodiment 72 is the compound or salt of any one of the embodiments 67-71, wherein $R_C$ is selected from the group consisting of hydroxyl, F, Cl, —CF$_3$, OCF$_3$, —O—C$_{1-6}$alkyl, and —C$_{1-6}$alkyl.

Embodiment 73 is the compound or salt of any one of the embodiments 67-72, wherein $R_C$ is selected from the group consisting of hydroxyl, F, Cl, —CF$_3$, —OCH$_3$, —OCF$_3$, —OCH$_2$CH$_3$, —OCH(CH$_3$)$_2$, —CH$_3$, —CH$_2$CH$_3$, —CH$_2$CH$_2$CH$_3$, and —CH(CH$_3$)$_2$.

Embodiment 74 is the compound or salt of any one of the embodiments 67-71, wherein $R_C$ is —C(O)OC$_{1-4}$ alkyl.

Embodiment 75 is the compound or salt of any one of the embodiments 67-71, wherein $R_C$ is selected from the group consisting of —CO$_2$CH$_3$, —CO$_2$CH$_2$CH$_3$, —CO$_2$CH(CH$_3$)$_2$, —CO$_2$CH$_2$CH$_2$CH$_3$, —CO$_2$CH$_2$CH$_2$CH$_2$CH$_3$, —CO$_2$—CH$_2$Ph, and —CO$_2$CH$_2$CH(CH$_3$)$_2$.

Embodiment 76 is the compound or salt of any one of the embodiments 67-75, wherein V is a covalent bond and Y is alkylene optionally interrupted by one or more —O— groups.

Embodiment 77 is the compound or salt of any one of the embodiments 67-76, wherein —V—Y— is —CH$_2$—, —CH$_2$CH$_2$—, —CH$_2$CH$_2$CH$_2$—, —CH$_2$CH$_2$CH$_2$CH$_2$—, —CH$_2$CH$_2$CH$_2$CH$_2$CH$_2$—, —CH$_2$CH$_2$CH$_2$CH$_2$CH$_2$CH$_2$—, or —CH$_2$CH$_2$—O—CH$_2$CH$_2$—.

Embodiment 78 is the compound or salt of any one of the embodiments 67-76, wherein —V—Y— is —O—C$_{1-7}$alkylene- or —C$_{1-8}$alkylene-.

Embodiment 79 is the compound or salt of any one of the embodiments 67-78, wherein R$_{2C}$ is selected from the group consisting hydrogen, alkyl, alkoxyalkylenyl, alkylaminoalkylenyl, and hydroxyalkylenyl.

Embodiment 80 is the compound or salt of any one of the embodiments 67-79, wherein R$_{2C}$ is selected from the group consisting of hydrogen, alkyl, and alkoxyalkylenyl.

Embodiment 81 is the compound or salt of any one of the embodiments 67-80, wherein R$_{2B}$ is selected from the group consisting of hydrogen, —CH$_3$, —CH$_2$CH$_3$, —CH$_2$CH$_2$CH$_3$, —CH$_2$CH$_2$CH$_2$CH$_3$, —CH$_2$OCH$_3$, —CH$_2$OCH$_2$CH$_3$, and —CH$_2$CH$_2$OCH$_3$.

Embodiment 82 is the compound or salt of any one of the embodiments 67-79, wherein R$_{2C}$ is selected from the group consisting of hydrogen, —CH$_3$, —CH$_2$CH$_3$, —CH$_2$CH$_2$CH$_3$, —CH$_2$CH$_2$CH$_2$CH$_3$, —CH$_2$OCH$_3$, —CH$_2$OCH$_2$CH$_3$, —CH$_2$CH$_2$OCH$_3$, —CH$_2$NHCH$_3$, —CH$_2$NHCH$_2$CH$_3$, —CH$_2$CH$_2$NHCH$_3$, —CH$_2$OH, and —CH$_2$CH$_2$OH.

Embodiment 83 is the compound or salt of any one of the embodiments 67-78, wherein R$_2$ is —CH$_2$NHOCH$_3$, —CH$_2$NHC(O)CH$_3$ or —CH$_2$NHC(O)cyclopropyl.

Embodiment 84 is the compound or salt of any one of the embodiments 67-83, wherein R$_{5C}$ and R$_{6C}$ are independently selected from the group consisting of hydrogen, alkyl, phenyl, and phenylalkylenyl, and wherein R$_{5C}$ and R$_{6C}$ are not both hydrogen.

Embodiment 85 is the compound or salt of any one of the embodiments 67-84, wherein R$_{5C}$ and R$_{6C}$ are independently selected from the group consisting of alkyl, phenyl, and phenylalkylenyl.

Embodiment 86 is the compound or salt of any one of the embodiments 67-85, wherein R$_{5C}$ is alkyl and R$_{6C}$ is alkyl.

Embodiment 87 is the compound or salt of any one of the embodiments 67-86, wherein R$_{5C}$ is C$_{1-8}$alkyl and R$_{6C}$ is C$_{1-8}$alkyl.

Embodiment 88 is the compound or salt of any one of the embodiments 67-87, wherein R$_{5C}$ is C$_{1-4}$alkyl and R$_{6C}$ is C$_{1-4}$alkyl.

Embodiment 89 is the compound or salt of any one of the embodiments 67-83, wherein R$_{5C}$ and R$_{6C}$ are independently selected from the group consisting of alkyl, cycloalkyl, aryl, arylalkylenyl, aryloxyalkylenyl, heteroaryl, heteroarylalkylenyl, heteroaryloxyalkylenyl, cycloalkylalkylenyl, aryl-(CH$_2$)$_{2-6}$—O-alkylenyl, and benzyloxyalkylenyl; wherein any of the alkyl, cycloalkyl, aryl, arylalkylenyl, aryloxyalkylenyl, heteroaryl, heteroarylalkylenyl, heteroaryloxyalkylenyl, cycloalkylalkylenyl, aryl-(CH$_2$)$_{2-6}$—O-alkylenyl, and benzyloxyalkylenyl groups can be either unsubstituted or substituted with one or more substituents independently selected from the group consisting of halogen, hydroxyl, alkoxy, alkyl, haloalkyl, cycloalkyl, nitrile, aryl, heteroaryl, and dialkylamino.

Embodiment 90 is the compound or salt of any one of the embodiments 67-83, wherein R$_{5C}$ and R$_{6C}$ are independently selected from the group consisting of hydrogen, —CH$_3$, —CH$_2$CH$_3$, —CH(CH$_3$)$_2$, —CH$_2$CH$_2$CH$_3$, —CH$_2$CH$_2$CH$_2$CH$_3$, —CH$_2$CH(CH$_3$)$_2$, —C(CH$_3$)$_3$, —CH$_2$CH$_2$CH$_2$CH$_2$CH$_3$, —(CH$_2$)$_{5-9}$CH$_3$, —CH$_2$CH$_2$CH(CH$_3$)$_2$, cyclopropyl, cyclopentyl, cyclohexyl, —CH$_2$-cyclopropyl, —CH$_2$-cyclopentyl, —CH$_2$-cyclohexyl, —CH$_2$CH$_2$—O—CH$_3$, —(CH$_2$)$_{3-8}$—O—CH$_3$, and —CH$_2$CH$_2$CH$_2$N(CH$_3$)$_2$; wherein R$_{5C}$ and R$_{6C}$ are not both hydrogen.

Embodiment 91 is the compound or salt of any one of the embodiments 67-83, wherein R$_{5C}$ and R$_{6C}$ are independently selected from the group consisting of hydrogen, alkyl, —CH$_2$Ph, —CH$_2$CH$_2$Ph, —CH$_2$CH$_2$—O-Ph, -Ph, —(CH$_2$)$_{3-8}$-Ph, —(CH$_2$)$_{3-8}$—O-Ph, —CH$_2$CH$_2$—O—CH$_2$Ph, —(CH$_2$)$_{3-8}$—O—CH$_2$Ph, and —(CH$_2$)$_{2-8}$—O—(CH$_2$)$_{1-4}$Ph, wherein the Ph group can be either unsubstituted or substituted with one or more substituents independently selected from the group consisting of halogen, hydroxyl, alkoxy, alkyl, haloalkyl, cycloalkyl, and nitrile; and wherein R$_{5C}$ and R$_{6C}$ are not both hydrogen.

Embodiment 92 is the compound or salt of embodiment 67, wherein V is selected from the group consisting of a covalent bond and —O—; Y is alkylene optionally interrupted by one or more —O— groups; q is an integer from 1 to 2; t is 1; R$_{2C}$ is selected from the group consisting of hydrogen, —CH$_3$, —CH$_2$CH$_3$, —CH$_2$CH$_2$CH$_3$, —CH$_2$CH$_2$CH$_2$CH$_3$, —CH$_2$OCH$_3$, —CH$_2$OCH$_2$CH$_3$, and —CH$_2$CH$_2$OCH$_3$.

Embodiment 93 is the compound or salt of any one of the embodiments 67-92, wherein the pharmaceutically acceptable salt is hydrochloride.

Embodiment 94 is the compound or salt of any one of the embodiments 66-92, wherein the pharmaceutically acceptable salt is dihydrochloride.

Embodiment 95 is a pharmaceutical composition comprising a therapeutically effective amount of a compound or salt of any one of the embodiments 67-94 in combination with a pharmaceutically acceptable carrier.

Embodiment 96 is a method of inducing cytokine biosynthesis in an animal comprising administering an effective amount of a compound or salt of any one of the embodiments 67-94 to the animal.

Embodiment 97 is a method of inducing biosynthesis of IFN-alpha in an animal comprising administering an effective amount of a compound or salt of any one of the embodiments 67-94 to the animal.

Embodiment 98 is a method of inducing biosynthesis of IFN-gamma in an animal comprising administering an effective amount of a compound or salt of any one of the embodiments 67-94 to the animal.

Embodiment 99 is a method of inducing biosynthesis of TNF-alpha in an animal comprising administering an effective amount of a compound or salt of any one of the embodiments 67-94 to the animal.

Embodiment 100 is a method of inducing biosynthesis of IP-10 in an animal comprising administering an effective amount of a compound or salt of any one of the embodiments 67-94 to the animal.

Objects and advantages of the disclosure are further illustrated by the examples provided herein. The particular materials and amounts thereof recited in these examples, as well as other conditions and details, are merely illustrative and are not intended to be limiting. The person of ordinary skill in the art, after carefully reviewing the entirety of this disclosure, will be able to use materials and conditions in addition to those specifically described in the examples.

EXAMPLES

Example 1

1-[4-(4-amino-2-butyl-imidazo[4,5-c]quinolin-1-yl)butyl]-3-isopropyl-guanidine dihydrochloride

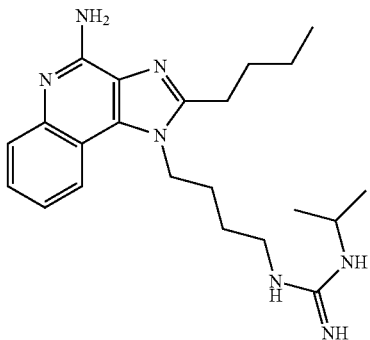 [SMILES: CCCCc1nc2c(N)nc3ccccc3c2n1CCCCNC(=N)NC(C)C]

1-(4-aminobutyl)-2-butyl-imidazo[4,5-c]quinolin-4-amine (2.14 g, 6.88 mmol) was suspended in 12 mL of anhydrous DMF and stirred under a nitrogen atmosphere. Diisopropylethylamine (1.32 mL, 7.65 mmol) and N-isopropylpyrazole-1-carboxamidine hydrochloride (1.44 g, 7.65 mmol) were then added and the reaction mixture was stirred for 3 days. The reaction mixture was then concentrated under reduced pressure to give a brown syrup. The syrup was triturated with acetonitrile to give a brown solid. Chromatography (SiO$_2$, chloroform-methanol-water-acetic acid eluent 80:18:2:0.1 with a gradient to 50:40:10:0.1) gave a foam. The foam was concentrated from 1N hydrochloric acid solution followed by ethanol to give a solid. The solid was dissolved in a minimum amount of methanol and then precipitated by the addition of acetonitrile. The resulting solid was isolated by filtration and dried to provide 1-[4-(4-amino-2-butyl-imidazo[4,5-c]quinolin-1-yl)butyl]-3-isopropyl-guanidine dihydrochloride as an off-white powder, mp 210-216° C. $^1$H NMR (CD$_3$OD, 500 MHz) 8.26 (m, 1H), 7.83 (m, 1H), 7.74 (m, 1H), 7.66 (m, 1H), 4.67 (t, J=7.7, 2H), 3.70 (m, 1H), 3.28 (t, J=6.9, 2H), 3.11 (t, J=7.7 Hz, 2H), 2.04-1.95 (m, 4H), 1.86-1.79 (m, 2H), 1.62-1.54 (m, 2H), 1.17 (d, J=6.4 Hz, 6H), 1.05 (t, J=7.4 Hz, 3H).

Example 2

1-[4-(4-amino-2-butyl-imidazo[4,5-c]quinolin-1-yl)butyl]-2,3-diisopropyl-guanidine Dihydrochloride

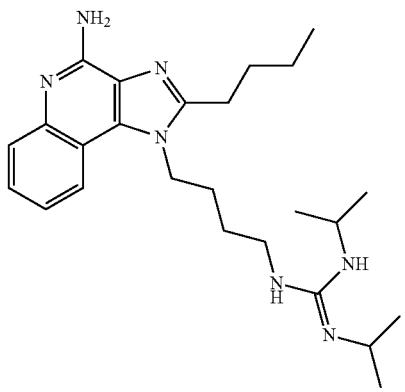 [SMILES: CCCCc1nc2c(N)nc3ccccc3c2n1CCCCN/C(=N/C(C)C)NC(C)C]

1-(4-aminobutyl)-2-butyl-imidazo[4,5-c]quinolin-4-amine (1.00 g, 3.22 mmol) was suspended in 12 mL of anhydrous DMF and stirred under a nitrogen atmosphere. Diisopropylcarbodiimide (0.51 mL, 3.3 mmol) was added and the reaction mixture was heated to 100° C. and stirred for 2 days. The reaction mixture was then concentrated under reduced pressure to give a brown syrup. Chromatography (SiO$_2$, chloroform-methanol-water-acetic acid eluent 80:18:2:0.1 with a gradient to 50:40:10:0.1) gave a foam. The foam was concentrated from 1N hydrochloric acid solution followed by ethanol to give a solid. Crystallization from acetonitrile-methanol provided 1-[4-(4-amino-2-butyl-imidazo[4,5-c]quinolin-1-yl)butyl]-2,3-diisopropyl-guanidine dihydrochloride as white crystals, mp 172-174° C. $^1$H NMR (CD$_3$OD, 500 MHz) 8.30 (m, 1H), 7.84 (m, 1H), 7.76 (m, 1H), 7.67 (m, 1H), 4.74 (t, J=7.6, 2H), 3.76 (m, 2H), 3.34 (t, J=7.0, 2H), 3.12 (t, J=7.7 Hz, 2H), 2.04-1.95 (m, 4H), 1.85-1.77 (m, 2H), 1.62-1.54 (m, 2H), 1.17 (d, J=6.4 Hz, 12H), 1.05 (t, J=7.4 Hz, 3H).

Cytokine Induction in Human Cells

Whole blood was obtained from healthy human donors and collected by venipuncture into vacutainer tubes or syringes containing EDTA. Human peripheral blood mononuclear cells (PBMC) were purified from the whole blood by density gradient centrifugation. Histopaque 1077 (15 mL, Sigma, St. Louis, Mo.) was transferred to 6×50 mL sterile polypropylene conical tubes. The Histopaque was overlayed with 15-25 mL of blood diluted 1:2 in Hank's Balanced Salts Solution (HBSS) (Gibco, Life Technology, Grand Island N.Y.). The tubes were then centrifuged at 1370 rpm for 30 minutes at 20° C., with no brake (400×g, GH 3.8 A Rotor).

The interface (buffy coat) containing the PBMC was collected and placed in a new sterile 50 mL conical polypropylene centrifuge tube. The PBMC were mixed with an equal volume of HBSS (about 20 mL from the interface and about 20 mL of HBSS), and then centrifuged at 1090 rpm, 10 min, 20° C., with brake (270×g, GH 3.8 A Rotor). After completing centrifugation, the cells were resuspended in 2-3 mL ACK Red blood cell lysis buffer (ammonium chloride potassium solution, Gibco, Life Technology) and incubated for 2-5 minutes at 20° C. Next, HBSS (40 mL) was added to the cells, and the sample was centrifuged at 270×g for 10 min at 20° C. The supernatant was decanted, and the cell pellet was resuspended in 5 mL AIM V® Medium (Gibco, Life Technology). Cell aggregates and debris were removed by filtering the cell solution through a BD Falcon 70 micron nylon cell strainer (BD Biosciences, San Jose, Calif.).

The number of viable cells were determined by counting with a Miltenyi FACS instrument (Miltenyi Biotec Inc., San Diego, Calif.) or by using a hemacytometer. For determining cell viability with a hemacytometer, the cells were diluted 1/10 in 0.4% trypan blue and HBSS (specifically, 50 microliter of trypan blue+40 microliter of HBSS+10 microliter of cell solution were added to a microfuge tube and mixed). Ten microliters of the diluted cells were then applied to the hemacytometer, and the number of viable PBMC were determined by microscopy.

The PBMC sample was then resuspended in 96-well plates at a concentration of 8×10$^5$ cells/well in 0.1 mL of AIM-V medium. Each compound was solubilized in DMSO to create a 3 mM stock solution. The stock solution was then further diluted with AIM-V medium to prepare the serial dilutions. The diluted compound (100 microliters) was then transferred to the PBMCs to achieve final compound concentrations of 10, 1, 0.1, 0.01, 0.001, 0.0001 micromolar. The plates also had both positive and negative controls. The negative control wells contained only AIM-V medium with no example compound. The positive control wells contained imiquimod serially diluted to concentrations of 10, 1, 0.1, 0.01, 0.001, 0.0001 micromolar. The plates were then cultured at 37'C/5% $CO_2$ for 21-24 hrs. Cell-free supernatants were harvested by centrifuging the 96-well plates at 2100 rpm, 23° C. for 10 minutes. Approximately 160 microliter of the supernatant was then stored in a NUNC 96-well plate, covered with the compression cap and stored at −80'C until the cytokine analysis was done.

IFN-alpha cytokine levels (pg/mL) were measured by ELISA (human IFN-α, pan specific, Mabtech, Cinncinnati, Ohio), IFN-gamma, TNF-alpha, and IP-10 cytokine levels (pg/mL) were measured by multiplex bead assay (magnetic beads, R & D Systems Minneapolis, Minn.) according to the manufacturer's instructions.

The data was analyzed to determine the minimum effective concentration (MEC) for each compound at which induction of a particular cytokine was observed in the assay. Specifically, the minimum effective concentration of each compound (micromolar) was determined as the lowest concentration of the compound that induced a measured cytokine response at a level (pictograms/mL) that was at least 2× greater than that observed with the negative control wells. The results are presented in Table 1.

TABLE 1

| | MEC to Induce Cytokine (micromolar) | | | |
|---|---|---|---|---|
| Compound | IFN-alpha | IFN-gamma | TNF-alpha | IP-10 |
| Example 1 | 0.01 | 0.1 | 0.1 | 0.001 |
| Example 2 | 0.1 | 1 | 10 | 0.1 |
| imiquimod | 10 | 10 | 10 | 10 |

NT = not tested

The complete disclosures of the patents, patent documents, and publications cited herein are incorporated by reference in their entirety as if each were individually incorporated. Various modifications and alterations to this invention will become apparent to those of ordinary skill in the art without departing from the scope and spirit of this invention. It should be understood that this invention is not intended to be unduly limited by the illustrative embodiments and examples set forth herein and that such examples and embodiments are presented by way of example only with the scope of the invention intended to be limited only by the claims set forth herein as follows.

I claim:
1. A compound of the Formula (I):

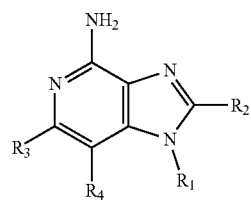

Formula I wherein:
$R_3$ and $R_4$ are taken together to form a fused benzene ring, a fused pyridine ring, a fused cyclohexene ring, or a fused tetrahydropyridine ring; wherein the fused benzene ring, fused pyridine ring, fused cyclohexene ring, or fused tetrahydropyridine ring is either unsubstituted or substituted by one or more R groups;

R is selected from the group consisting of halogen, hydroxyl, alkyl, alkoxy, haloalkyl, —C(O)—O-alkyl, —C(O)—O—$CH_2$Ph, —C(O)—O-aryl, amino, alkylamino, and dialkylamino aryl, arylalkylenyl, aryloxyalkylenyl, arylalkyleneoxy, aryloxy, heteroaryl, heteroarylalkylenyl, heteroaryloxyalkyenyl, heteroarylalkyleneoxy, and heteroaryloxy, wherein the alkyl, aryl, arylalkylenyl, aryloxyalkylenyl, arylalkyleneoxy, aryloxy, heteroaryl, heteroarylalkylenyl, heteroaryloxyalkyenyl, heteroarylalkyleneoxy, and heteroaryloxy groups can be unsubstituted or substituted by one or more substituents independently selected from the group consisting of alkyl, alkoxy, halogen, haloalkyl, hydroxyl, hydroxyalkylenyl, alkoxyalkylenyl, arylalkyleneoxy, and nitrile;

$R_1$ is selected from the group consisting of —W—X—N($R_7$)—C(=N—$R_5$)—N(H)$R_6$, —W—Z—N($R_7$)—C(=N—$R_5$)—N(H)$R_6$, and

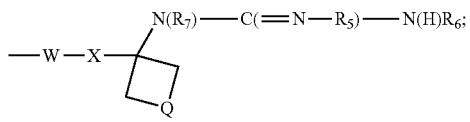

W is selected from the group consisting of a covalent bond, —O—, and NH—;
X is selected from the group consisting of alkylene, alkenylene, and alkynylene, wherein any of the alkylene, alkenylene, and alkynylene groups can be optionally interrupted by one or more —O— groups;
Z is selected from the group consisting of
—X-arylene-X—,
—X-heteroarylene-X—,
—X-arylene-, and
—X-heteroarylene-;
$R_2$ is selected from the group consisting of hydrogen, alkyl, alkenyl, alkynyl, —O-alkyl, hydroxyalkylenyl, alkoxyalkylenyl, alkylaminoalkylenyl, hydroxyl, —$CH_2$—NH—O-alkyl, and —$CH_2$NHC(O)-alkyl;
$R_7$ is selected from the group consisting of hydrogen, alkyl, arylalkylenyl, alkoxyalkylenyl, aryloxyalkylenyl, benzyloxyalkylenyl, aryl-$(CH_2)_{2-6}$—O-alkylenyl, and cycloalkylalkylenyl; wherein any of the alkyl, arylalkylenyl, alkoxyalkylenyl, aryloxyalkylenyl, benzyloxyalkylenyl, aryl-$(CH_2)_{2-6}$—O-alkylenyl, and cycloalkylalkylenyl groups can be either unsubstituted or substituted with one or more substituents selected from the group consisting of halogen, hydroxyl, alkyl, alkoxy, haloalkyl, and nitrile;
$R_5$ and $R_6$ are independently selected from the group consisting of hydrogen, —C(O)—O-alkyl, alkyl, cycloalkyl, aryl, arylalkylenyl, aryloxyalkylenyl, heteroaryl, heteroarylalkylenyl, heteroaryloxyalkylenyl, cycloalkylalkylenyl, aryl-$(CH_2)_{2-6}$—O-alkylenyl, and benzyloxyalkylenyl; wherein any of the alkyl, cycloalkyl, aryl, arylalkylenyl, aryloxyalkylenyl, heteroaryl, heteroarylalkylenyl, heteroaryloxyalkylenyl, cycloalkylalkylenyl, aryl-$(CH_2)_{2-6}$—O-alkylenyl, and benzyloxyalkylenyl groups can be either unsubstituted or substituted with one or more substituents independently selected from the group consisting of halogen, hydroxyl, alkoxy, alkyl, haloalkyl, cycloalkyl, nitrile, aryl, heteroaryl, and dialkylamino; with the proviso that $R_5$ and $R_6$ are not both hydrogen;

Q is selected from the group consisting of a covalent bond, —$CH_2$—, —$CH_2CH_2$—, —$CH_2CH_2CH_2$—, —$CH_2CH_2CH_2CH_2$—, —$CH_2CH_2CH_2CH_2CH_2$—, —$CH_2$—O—$CH_2$—, and —$OCH_2$—;

or a pharmaceutically acceptable salt thereof.

2. The compound or salt of claim 1, wherein $R_7$ is hydrogen.

3. The compound or salt of claim 1, wherein W is a covalent bond or —O—.

4. The compound or salt of claim 1, wherein X is alkylene optionally interrupted by one or more —O— groups.

5. The compound or salt of claim 1, wherein Z is —$C_{1-5}$alkylene-arylene-$C_{1-5}$alkylene- or —$C_{1-5}$alkylene-heteroarylene-$C_{1-5}$alkylene-.

6. The compound or salt of claim 1, wherein $R_2$ is selected from the group consisting hydrogen, alkyl, alkoxyalkylenyl, alkylaminoalkylenyl, and hydroxyalkylenyl.

7. The compound or salt of claim 1, wherein $R_5$ and $R_6$ are independently selected from the group consisting of hydrogen, alkyl, phenyl, and phenylalkylenyl, and wherein $R_5$ and $R_6$ are not both hydrogen.

8. A compound of the Formula XIII:

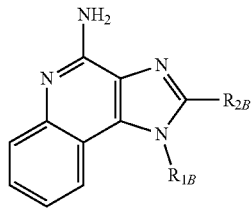

Formula XIII wherein:

$R_{1B}$ is selected from the group consisting of —$X_B$—N($R_{7B}$)—C(=N—$R_{5B}$)—N(H)$R_{6B}$, and —$Z_B$—N($R_{7B}$)—C(=N—$R_{5B}$)—N(H)$R_{6B}$, and

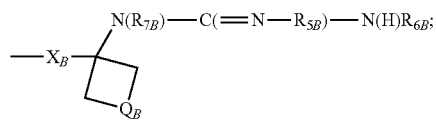

$X_B$ is selected from the group consisting of alkylene, alkenylene, and alkynylene, wherein the alkylene, alkenylene, and alkynylene groups can be optionally interrupted by one or more —O— groups;

$Z_B$ is selected from the group consisting of
—$X_B$-arylene-$X_B$—,
—$X_B$-heteroarylene-$X_B$—,
—$X_B$-arylene-, and
—$X_B$-heteroarylene-;

$R_{2B}$ is selected from the group consisting of hydrogen, alkyl, alkenyl, alkynyl, —O-alkyl, hydroxyalkylenyl, alkoxyalkylenyl, alkylaminoalkylenyl, hydroxyl, —$CH_2$—NH—O-alkyl, and —$CH_2$NHC(O)-alkyl;

$R_{7B}$ is selected from the group consisting of hydrogen, alkyl, arylalkylenyl, alkoxyalkylenyl, aryloxyalkylenyl, benzyloxyalkylenyl, aryl-$(CH_2)_{2-6}$—O-alkylenyl, and cycloalkylalkylenyl; wherein any of the alkyl, arylalkylenyl, alkoxyalkylenyl, aryloxyalkylenyl, benzyloxyalkylenyl, aryl-$(CH_2)_{2-6}$—O-alkylenyl, and cycloalkylalkylenyl groups can be either unsubstituted or substituted with one or more substituents selected from the group consisting of halogen, hydroxyl, alkyl, alkoxy, haloalkyl, and nitrile;

$R_{5B}$ and $R_{6B}$ are independently selected from the group consisting of hydrogen, —C(O)—O-alkyl, alkyl, cycloalkyl, aryl, arylalkylenyl, aryloxyalkylenyl, heteroaryl, heteroarylalkylenyl, heteroaryloxyalkylenyl, cycloalkylalkylenyl, aryl-$(CH_2)_{2-6}$—O-alkylenyl, and benzyloxyalkylenyl; wherein any of the, cycloalkyl, aryl, arylalkylenyl, aryloxyalkylenyl, heteroaryl, heteroarylalkylenyl, heteroaryloxyalkylenyl, cycloalkylalkylenyl, aryl-$(CH_2)_{2-6}$—O-alkylenyl, and benzyloxyalkylenyl groups can be either unsubstituted or substituted with one or more substituents independently selected from the group consisting of halogen, hydroxyl, alkoxy, alkyl, haloalkyl, cycloalkyl, nitrile, aryl, heteroaryl, and dialkylamino; with the proviso that $R_{5B}$ and $R_{6B}$ are not both hydrogen;

QB is selected from the group consisting of a covalent bond, —$CH_2$—, —$CH_2CH_2$—, —$CH_2CH_2CH_2$—, —$CH_2CH_2CH_2CH_2$—, —$CH_2CH_2CH_2CH_2CH_2$—, —$CH_2$—O—$CH_2$—, and —$OCH_2$—;

or a pharmaceutically acceptable salt thereof.

9. The compound or salt of claim 8, wherein $R_{7B}$ is hydrogen.

10. The compound or salt of claim 8, wherein $X_B$ is alkylene optionally interrupted by one or more —O— groups.

11. The compound or salt of claim 8, wherein $X_B$ is selected from the group consisting of $CH_2CH_2$—, —$CH_2CH_2CH_2$—, —$CH_2CH_2CH_2CH_2$—, —$CH_2CH_2CH_2CH_2CH_2$—, —$CH_2CH_2CH_2CH_2CH_2CH_2$—, —$CH_2CH_2CH_2CH_2CH_2CH_2CH_2$—, —$CH_2CH_2CH_2CH_2CH_2CH_2CH_2CH_2$—, —$CH_2C(CH_3)_2$—, —$CH_2C(CH_3)_2CH_2$—, —$CH_2CH_2$—O—$CH_2CH_2$—, —$CH_2CH_2$—O—$CH_2CH_2$—O—$CH_2CH_2$—, —$(CH_2)_{2-4}$—$(OCH_2CH_2-)_{1-5}$, and —$(CH_2)_{2-6}$—$(OCH_2CH_2-)_{1-4}$.

12. The compound or salt of claim 8, wherein $Z_B$ is —$C_{1-5}$alkylene-arylene-$C_{1-5}$alkylene- or —$C_{1-5}$alkylene-heteroarylene-$C_{1-5}$alkylene-.

13. The compound or salt of claim 8, wherein $Z_B$ is —$CH_2$-phenylene-$CH_2$—.

14. The compound or salt of claim 8, wherein $R_{2B}$ is selected from the group consisting hydrogen, alkyl, alkoxyalkylenyl, alkylaminoalkylenyl, and hydroxyalkylenyl.

15. The compound or salt of claim 8, wherein $R_{2B}$ is selected from the group consisting of hydrogen, —$CH_3$, —$CH_2CH_3$, —$CH_2CH_2CH_3$, —$CH_2CH_2CH_2CH_3$, —$CH_2OCH_3$, —$CH_2OCH_2CH_3$, and —$CH_2CH_2OCH_3$.

16. The compound or salt of claim 8, wherein $R_{5B}$ and $R_{6B}$ are independently selected from the group consisting of hydrogen, alkyl, phenyl, phenylalkylenyl; and wherein $R_{5B}$ and $R_{6B}$ are not both hydrogen.

17. The compound or salt of claim 8, wherein $R_{5B}$ and $R_{6B}$ are independently selected from the group consisting of alkyl, phenyl, and phenylalkylenyl.

18. The compound or salt of claim 8, wherein $R_{5B}$ is alkyl and $R_{6B}$ is alkyl.

19. A method of inducing biosynthesis of IFN-alpha in an animal comprising administering an effective amount of a compound or salt of claim 1 to the animal.

20. A pharmaceutical composition comprising a therapeutically effective amount of a compound or salt of claim 1 in combination with a pharmaceutically acceptable carrier.

* * * * *

UNITED STATES PATENT AND TRADEMARK OFFICE
CERTIFICATE OF CORRECTION

PATENT NO. : 10,118,925 B2
APPLICATION NO. : 15/753573
DATED : November 6, 2018
INVENTOR(S) : George Griesgraber Page 1 of 3

It is certified that error appears in the above-identified patent and that said Letters Patent is hereby corrected as shown below:

On the Title Page

Column 2, (Abstract)
Line 1, Delete "imidzao[4,5-" and insert -- imidazo[4,5- --, therefor.

In the Specification

Column 1
Line 30 (Approx.), Delete "]naphthyidin" and insert -- ]naphthyridin --, therefor.

Column 3
Line 63-64, Delete "bomyl, norbomyl, norbomenyl, and the like" and insert -- bornyl, norbornyl, norbornenyl, and the like. --, therefor.

Column 4
Line 52, Delete "napthyridinyl, ixoxazolyl," and insert -- naphthyridine, isoxazolyl, --, therefor.

Column 6
Line 27-28 (Approx.), Delete "heteroaryloxyalkyenyl," and insert -- heteroaryloxyalkylenyl, --, therefor.
Line 30-31 (Approx.), Delete "heteroaryloxyalkyenyl," and insert -- heteroaryloxyalkylenyl, --, therefor.

Column 9
Line 33, Delete "benyloxyalkylenyl" and insert -- benzyloxyalkylenyl --, therefor.

Column 12
Line 12-13, Delete "heteroaryloxyalkyenyl," and insert -- eteroaryloxyalkylenyl, --, therefor.
Line 16, Delete "heteroaryloxyalkyenyl," and insert -- heteroaryloxyalkylenyl, --, therefor.

Signed and Sealed this
Fourteenth Day of May, 2019

Andrei Iancu
*Director of the United States Patent and Trademark Office*

Column 16
Line 51, Delete "C2-8alky-" and insert -- C2-5alky- --, therefor.

Column 17
Line 3-4, Delete "In some embodiments of Formula XIII, R1B is —XB—(H)—
C(=N—R5B)—N(H)R6B." and insert the same on Column 17, Line 4, as a new paragraph.

Column 19
Line 2-3, Delete "heteroaryloxyalkyenyl," and insert -- heteroaryloxyalkylenyl, --, therefor.
Line 6, Delete "heteroaryloxyalkyenyl," and insert -- heteroaryloxyalkylenyl, --, therefor.

Column 23
Line 11-12, Delete "diisopropylcabodiimide" and insert -- diisopropylcarbodiimide --, therefor.

Column 28
Line 16 (Approx.), Delete "(rig/kg)" and insert -- (μg/kg) --, therefor.

Column 29
Line 51, Delete "picomavirus" and insert -- picornavirus --, therefor.

Column 30
Line 28, Delete "haepatitis" and insert -- hepatitis --, therefor.
Line 33, Delete "hemophilus" and insert -- haemophilus --, therefor.

Column 32
Line 27-28 (Approx.), Delete "heteroaryloxyalkyenyl," and insert -- heteroaryloxyalkylenyl, --, therefor.
Line 31 (Approx.), Delete "heteroaryloxyalkyenyl," and insert -- heteroaryloxyalkylenyl, --, therefor.

Column 39
Line 43-44, Delete "heteroaryloxyalkyenyl," and insert -- heteroaryloxyalkylenyl, --, therefor.
Line 47, Delete "heteroaryloxyalkyenyl," and insert -- heteroaryloxyalkylenyl, --, therefor.

Column 45
Line 4, Delete "37'C/5%" and insert -- 37° C./5% --, therefor.
Line 8, Delete "-80'C" and insert -- -80° C. --, therefor.
Line 12, Delete "Cinncinnati," and insert -- Cincinnati, --, therefor.

In the Claims

Column 46
Line 9-10 (Approx.), In Claim 1, delete "heteroaryloxyalkyenyl," and insert
-- heteroaryloxyalkylenyl, --, therefor.
Line 13 (Approx.), In Claim 1, delete "heteroaryloxyalkyenyl," and insert
-- heteroaryloxyalkylenyl, --, therefor.
Line 13-14 (Approx.), In Claim 1, delete "heteroaryalkyleneoxy," and insert -- heteroarylalkyleneoxy, --, therefor.
Line 31, In Claim 1, delete "NH—;" and insert -- —NH—; --, therefor.

Column 48
Line 36, In Claim 11, delete "CH2CH2—," and insert -- —CH2CH2—, --, therefor.